US008123703B2

(12) United States Patent  
Martin et al.

(10) Patent No.: US 8,123,703 B2
(45) Date of Patent: Feb. 28, 2012

(54) STEERABLE ACCESS SHEATH AND METHODS OF USE

(75) Inventors: Brian B. Martin, Boulder Creek, CA (US); Amy R. Raatikka, San Francisco, CA (US); Troy L. Thornton, San Francisco, CA (US); Ferolyn T. Powell, San Francisco, CA (US)

(73) Assignee: Evalve, Inc., Menlo Park, CA (US)

( * ) Notice: Subject to any disclaimer, the term of this patent is extended or adjusted under 35 U.S.C. 154(b) by 41 days.

(21) Appl. No.: 12/699,759

(22) Filed: Feb. 3, 2010

(65) Prior Publication Data

US 2010/0130924 A1   May 27, 2010

Related U.S. Application Data

(60) Continuation of application No. 12/392,670, filed on Feb. 25, 2009, now Pat. No. 7,682,319, and a division of application No. 10/441,753, filed on May 19, 2003, now abandoned, which is a continuation-in-part of application No. 09/894,463, filed on Jun. 27, 2001, now Pat. No. 6,752,813, which is a continuation-in-part of application No. 09/544,930, filed on Apr. 7, 2000, now Pat. No. 6,629,534.

(60) Provisional application No. 60/128,690, filed on Apr. 9, 1999.

(51) Int. Cl.
*A61M 25/00* (2006.01)

(52) U.S. Cl. ....................................... 600/585

(58) Field of Classification Search .............. 600/585; 604/164.13, 165.01, 523
See application file for complete search history.

(56) References Cited

U.S. PATENT DOCUMENTS

| | | | |
|---|---|---|---|
| 2,097,018 | A | 10/1937 | Chamberlain |
| 2,108,206 | A | 2/1938 | Meeker |
| 3,296,668 | A | 1/1967 | Aiken |
| 3,378,010 | A | 4/1968 | Codling |

(Continued)

FOREIGN PATENT DOCUMENTS

DE   3504292   7/1986

(Continued)

OTHER PUBLICATIONS

Abe et al., "De Vega's annuloplasty for acquired tricuspid disease: Early and late results in 110 patients" Ann. Thorac. Surg. (1989) 48:670-676.

(Continued)

*Primary Examiner* — Jeffrey G Hoekstra
(74) *Attorney, Agent, or Firm* — Sughrue Mion, PLLC; Jonathan Feuchtwang

(57) ABSTRACT

The present invention provides devices, systems, methods and kits for endoscopically accessing a body cavity and providing a directed pathway toward a target tissue within the cavity. The directed pathway is provided by an access sheath which is positioned in a desired configuration, generally directed toward the target tissue. Depending on the location of the target tissue and the desired angle of approach, the access sheath may be required to maintain one or more curves in one or more planes to properly direct the interventional devices. In addition, the access sheath has a locking feature to hold the sheath in place and maintain the desired configuration. Interventional devices may then be passed through the sheath to the target tissue.

30 Claims, 18 Drawing Sheets

U.S. PATENT DOCUMENTS

| | | |
|---|---|---|
| 3,557,780 A | 1/1971 | Sato |
| 3,671,979 A | 6/1972 | Moulopouslos |
| 3,874,388 A | 4/1975 | King et al. |
| 4,007,743 A | 2/1977 | Blake |
| 4,056,854 A | 11/1977 | Boretos et al. |
| 4,064,881 A | 12/1977 | Meredith |
| 4,112,951 A | 9/1978 | Hulka et al. |
| 4,235,238 A | 11/1980 | Ogiu et al. |
| 4,297,749 A | 11/1981 | Davis et al. |
| 4,425,908 A | 1/1984 | Simon |
| 4,458,682 A | 7/1984 | Cerwin |
| 4,484,579 A | 11/1984 | Meno et al. |
| 4,487,205 A | 12/1984 | Di Giovanni et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,686,965 A | 8/1987 | Bonnet et al. |
| 4,777,951 A | 10/1988 | Cribier et al. |
| 4,809,695 A | 3/1989 | Gwathmey et al. |
| 4,917,089 A | 4/1990 | Sideris |
| 4,944,295 A | 7/1990 | Gwathmey et al. |
| 4,969,890 A | 11/1990 | Sugita et al. |
| 4,994,077 A | 2/1991 | Dobben |
| 5,015,249 A | 5/1991 | Nakao et al. |
| 5,019,096 A | 5/1991 | Fox, Jr. et al. |
| 5,042,707 A | 8/1991 | Taheri |
| 5,047,041 A | 9/1991 | Samuels |
| 5,049,153 A | 9/1991 | Nakao et al. |
| 5,061,277 A | 10/1991 | Carpentier et al. |
| 5,069,679 A | 12/1991 | Taheri |
| 5,108,368 A | 4/1992 | Hammerslag et al. |
| 5,125,758 A | 6/1992 | DeWan |
| 5,171,252 A | 12/1992 | Friedland |
| 5,171,259 A | 12/1992 | Inoue |
| 5,190,554 A | 3/1993 | Coddington, III et al. |
| 5,195,968 A | 3/1993 | Lundquist et al. |
| 5,209,756 A | 5/1993 | Seedhom et al. |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,330,442 A | 7/1994 | Green et al. |
| 5,332,402 A | 7/1994 | Teitelbaum |
| 5,350,397 A | 9/1994 | Palermo et al. |
| 5,350,399 A | 9/1994 | Erlebacher et al. |
| 5,359,994 A | 11/1994 | Krauter et al. |
| 5,368,564 A | 11/1994 | Savage |
| 5,368,601 A | 11/1994 | Sauer et al. |
| 5,383,886 A | 1/1995 | Kensey et al. |
| 5,403,312 A | 4/1995 | Yates et al. |
| 5,403,326 A | 4/1995 | Harrison et al. |
| 5,411,552 A | 5/1995 | Andersen et al. |
| 5,417,699 A | 5/1995 | Klein et al. |
| 5,417,700 A | 5/1995 | Egan |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,476,470 A | 12/1995 | Fitzgibbons |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,507,725 A | 4/1996 | Savage et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,593,424 A | 1/1997 | Northrup, III |
| 5,593,435 A | 1/1997 | Carpentier et al. |
| 5,609,598 A | 3/1997 | Laufer et al. |
| 5,618,306 A | 4/1997 | Roth et al. |
| 5,620,452 A | 4/1997 | Yoon |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 5,690,671 A | 11/1997 | McGurk et al. |
| 5,695,504 A | 12/1997 | Gifford, III et al. |
| 5,695,505 A | 12/1997 | Yoon |
| 5,702,825 A | 12/1997 | Keital et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racene et al. |
| 5,715,817 A | 2/1998 | Stevens-Wright et al. |
| 5,716,367 A | 2/1998 | Koike et al. |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,280 A | 4/1998 | Fleenor |
| 5,749,828 A | 5/1998 | Solomon et al. |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,592 A | 10/1998 | Hammerslag |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |

| | | |
|---|---|---|
| 5,843,031 A | 12/1998 | Hermann et al. |
| 5,849,019 A | 12/1998 | Yoon |
| 5,853,422 A | 12/1998 | Huebsch et al. |
| 5,855,271 A | 1/1999 | Eubanks et al. |
| 5,855,614 A | 1/1999 | Stevens et al. |
| 5,860,990 A | 1/1999 | Nobles et al. |
| 5,868,733 A | 2/1999 | Ockuly et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson, IV et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhardt et al. |
| 5,972,020 A | 10/1999 | Carpentier et al. |
| 5,972,030 A | 10/1999 | Garrison et al. |
| 5,980,455 A | 11/1999 | Daniel et al. |
| 5,989,284 A | 11/1999 | Laufer |
| 6,015,417 A | 1/2000 | Reynolds, Jr. |
| 6,019,722 A | 2/2000 | Spence et al. |
| 6,022,360 A | 2/2000 | Reimels et al. |
| 6,033,378 A | 3/2000 | Lundquist et al. |
| 6,036,699 A | 3/2000 | Andreas et al. |
| 6,048,351 A | 4/2000 | Gordon et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,086,600 A | 7/2000 | Kortenbach |
| 6,088,889 A | 7/2000 | Luther et al. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,143,024 A | 11/2000 | Campbell et al. |
| 6,159,240 A | 12/2000 | Sparer et al. |
| 6,162,233 A | 12/2000 | Williamson, IV et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,182,664 B1 | 2/2001 | Cosgrove |
| 6,187,003 B1 | 2/2001 | Buysse et al. |
| 6,190,408 B1 | 2/2001 | Melvin |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,245,079 B1 | 6/2001 | Nobles et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,669 B1 | 7/2002 | Frazier et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,508,828 B1 | 1/2003 | Akerfeldt et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Homer |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen, III et al. |
| 7,011,669 B2 | 3/2006 | Kimblad |
| 7,048,754 B2 | 5/2006 | Martin et al. |
| 7,112,207 B2 | 9/2006 | Allen et al. |
| 7,226,467 B2 | 6/2007 | Lucatero et al. |
| 7,288,097 B2 | 10/2007 | Séguin |
| 7,381,210 B2 | 6/2008 | Zarbatany et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,651,502 B2 | 1/2010 | Jackson |
| 7,682,319 B2 | 3/2010 | Martin et al. |
| 2001/0004715 A1 | 6/2001 | Duran et al. |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |

| | | |
|---|---|---|
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055774 A1 | 5/2002 | Liddicoat |
| 2002/0055775 A1 | 5/2002 | Carpentier et al. |
| 2002/0058910 A1 | 5/2002 | Hermann |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hilavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183835 A1 | 12/2002 | Taylor et al. |
| 2003/0045778 A1* | 3/2003 | Ohline et al. .................. 600/114 |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0088047 A1 | 5/2004 | Spence et al. |
| 2004/0092962 A1 | 5/2004 | Thorton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goar et al. |
| 2005/0021057 A1 | 1/2005 | St. Goar et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0149014 A1 | 7/2005 | Hauck et al. |
| 2005/0159810 A1 | 7/2005 | Filsoufi |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0015003 A1 | 1/2006 | Moaddes et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Rahdert et al. |
| 2007/0038293 A1 | 2/2007 | St.Goar et al. |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0198082 A1 | 8/2007 | Kapadia et al. |
| 2008/0039935 A1 | 2/2008 | Buch et al. |
| 2008/0051703 A1 | 2/2008 | Thornton et al. |
| 2008/0051807 A1 | 2/2008 | St. Goar et al. |
| 2008/0097489 A1 | 4/2008 | Goldfarb et al. |
| 2008/0167714 A1 | 7/2008 | St. Goar et al. |
| 2008/0183194 A1 | 7/2008 | Goldfarb et al. |
| 2009/0163934 A1 | 6/2009 | Raschdorf, Jr. et al. |
| 2009/0177266 A1 | 7/2009 | Powell et al. |
| 2009/0198322 A1 | 8/2009 | Deem et al. |
| 2009/0270858 A1 | 10/2009 | Hauck et al. |
| 2009/0326567 A1 | 12/2009 | Goldfarb et al. |
| 2010/0016958 A1 | 1/2010 | St. Goar et al. |
| 2010/0022823 A1 | 1/2010 | Goldfarb et al. |

FOREIGN PATENT DOCUMENTS

| | | |
|---|---|---|
| EP | 0 179 562 A1 | 4/1986 |
| EP | 0 179 562 B1 | 7/1989 |
| EP | 0 558 031 | 2/1993 |

| | | |
|---|---|---|
| EP | 0 684 012 | 11/1995 |
| EP | 0 727 239 | 8/1996 |
| EP | 1 674 040 | 6/2006 |
| FR | 2768324 | 3/1999 |
| GB | 1598111 | 9/1981 |
| GB | 2151142 | 7/1985 |
| JP | 59-85653 A | 5/1984 |
| JP | 09-253030 A | 9/1997 |
| JP | 11-089937 | 4/1999 |
| JP | 2000-283130 A | 10/2000 |
| WO | WO 81/00668 | 3/1981 |
| WO | WO 91/01689 | 2/1991 |
| WO | WO 92/12690 | 8/1992 |
| WO | WO 94/18881 | 9/1994 |
| WO | WO 94/18893 | 9/1994 |
| WO | WO 95/15715 A1 | 6/1995 |
| WO | WO 96/14032 A1 | 5/1996 |
| WO | WO 96/22735 | 8/1996 |
| WO | WO 96/30072 A1 | 10/1996 |
| WO | 97/18746 A2 | 5/1997 |
| WO | WO 97/18746 A2 | 5/1997 |
| WO | WO 97/25927 A1 | 7/1997 |
| WO | WO 97/26034 A1 | 7/1997 |
| WO | WO 97/38748 A2 | 10/1997 |
| WO | WO 97/39688 | 10/1997 |
| WO | WO 97/48436 A2 | 12/1997 |
| WO | WO 98/07375 | 2/1998 |
| WO | WO 98/24372 | 6/1998 |
| WO | WO 98/30153 | 7/1998 |
| WO | WO 98/32382 | 7/1998 |
| WO | WO 98/35638 | 8/1998 |
| WO | WO 99/00059 | 1/1999 |
| WO | WO 99/07354 | 2/1999 |
| WO | WO 99/13777 A1 | 3/1999 |
| WO | WO 99/66967 A1 | 12/1999 |
| WO | WO 00/02489 | 1/2000 |
| WO | WO 00/03651 A1 | 1/2000 |
| WO | WO 00/03759 | 1/2000 |
| WO | WO 00/12168 A1 | 3/2000 |
| WO | WO 00/44313 A1 | 8/2000 |
| WO | WO 00/59382 | 10/2000 |
| WO | WO 00/60995 | 10/2000 |
| WO | WO 01/00111 | 1/2001 |
| WO | WO 01/00114 A1 | 1/2001 |
| WO | WO 01/03651 A2 | 1/2001 |
| WO | WO 01/26557 | 4/2001 |
| WO | WO 01/26586 | 4/2001 |
| WO | WO 01/26587 A1 | 4/2001 |
| WO | WO 01/26588 A2 | 4/2001 |
| WO | WO 01/26703 A1 | 4/2001 |
| WO | WO 01/28432 | 4/2001 |
| WO | WO 01/28455 | 4/2001 |
| WO | WO 01/47438 A1 | 7/2001 |
| WO | WO 01/49213 A2 | 7/2001 |
| WO | WO 01/49213 A3 | 7/2001 |
| WO | WO 01/50985 A1 | 7/2001 |
| WO | WO 01/54618 | 8/2001 |
| WO | WO 01/56512 A1 | 8/2001 |
| WO | WO 01/66001 | 9/2001 |
| WO | WO 01/70320 A1 | 9/2001 |
| WO | WO 01/89440 A2 | 11/2001 |
| WO | WO 01/95831 A2 | 12/2001 |
| WO | WO 01/95832 A2 | 12/2001 |
| WO | WO 01/97741 A2 | 12/2001 |
| WO | WO 02/00099 A2 | 1/2002 |
| WO | WO 02/01999 A2 | 1/2002 |
| WO | WO 02/03892 | 1/2002 |
| WO | WO 02/34167 A2 | 5/2002 |
| WO | WO 02/34167 A3 | 5/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 03/001893 | 1/2003 |
| WO | WO 03/003930 A1 | 1/2003 |
| WO | WO 03/020179 | 3/2003 |
| WO | WO 03/028558 | 4/2003 |
| WO | WO 03/037171 | 5/2003 |
| WO | WO 03/047467 | 6/2003 |
| WO | WO 03/049619 | 6/2003 |
| WO | WO 03/073910 | 9/2003 |
| WO | WO 03/073913 | 9/2003 |
| WO | WO 03/105667 | 12/2003 |
| WO | WO 2004/004607 | 1/2004 |
| WO | WO 2004/012583 | 2/2004 |
| WO | WO 2004/012789 A2 | 2/2004 |
| WO | WO 2004/014282 A2 | 2/2004 |
| WO | WO 2004/019811 | 3/2004 |
| WO | WO 2004/030570 | 4/2004 |
| WO | WO 2004/037317 | 5/2004 |
| WO | WO 2004/045370 | 6/2004 |
| WO | WO 2004/045378 | 6/2004 |
| WO | WO 2004/045463 | 6/2004 |
| WO | WO 2004/047679 | 6/2004 |
| WO | WO 2004/062725 | 7/2004 |
| WO | WO 2004/082523 | 9/2004 |
| WO | WO 2004/082538 | 9/2004 |
| WO | WO 2004/093730 | 11/2004 |
| WO | WO 2004/112585 | 12/2004 |
| WO | WO 2004/112651 | 12/2004 |
| WO | WO 2005/002424 | 1/2005 |
| WO | WO 2005/018507 | 3/2005 |
| WO | WO 2005/027797 | 3/2005 |
| WO | WO 2005/032421 | 4/2005 |
| WO | WO 2005/062931 | 7/2005 |
| WO | WO 2005/112792 | 12/2005 |
| WO | WO 2006/105008 | 10/2006 |
| WO | WO 2006/105009 | 10/2006 |
| WO | WO 2006/115875 | 11/2006 |
| WO | WO 2006/115876 | 11/2006 |

OTHER PUBLICATIONS

Abe et al., "Updated: De Vega's annuloplasty for acquired tricuspid disease: Early and late results in 110 patients" Ann. Thorac. Surg. (1996) 62:1876-1877.

Agricola et al., "Mitral valve reserve in double orifice technique: an exercise echocardiographic study," Journal of Heart Valve Disease, (2002)11(5):637 643.

Alfieri, et al., "An effective technique to correct anterior mitral leaflet prolapse," J Card Surg, 1999; 14(6):468-470.

Alfieri et al., "Novel suture device for beating heart mitral leaflet approximation," Annals of Thoracic Surgery, (2002)74:1488 1493.

Alfieri et al., "The double orifice technique in mitral valve repair: a simple solution for complex problems," Journal of Thoracic Cardiovascular Surgery, (2001)122:674 681.

Alfieri et al., "The edge to edge technique," The European Association for Cardio Thoracic Surgry 14th Annual Meeting, Oct. 7-11, 2000 Book of Proceedings.

Alfieri , "The edge-to-edge repair of the mitral valve," [Abstract] 6th Annual NewEra Cardiac Care: Innovation & Technology, Heart Surgery Forum, (2003) pp. 103.

Alvarez et al., "Repairing the degenerative mitral valve: Ten- to fifteen-year follow-up" J. Thorac. Cardiovasc. Surg. (1996) 112:238-247.

Arisi et al., "Mitral valve repair with Alfieri technique in mitral regurgitation of diverse etiology: early echocardiographic results," Circulation Supplement II, (2001) 104(17):3240.

Bach et al., "Early improvement in congestive heart failure after correction of secondary mitral regurgitation in end-stage cardiomyopathy," Am. Heart J., (1995) 129:1165-1170.

Bach et al., "Improvement following correction of secondary mitral regurgitation in end-stage cardiomyopathy with mitral annuloplasty" Am. J. Cardiol., (1996) 78:966-969.

Bailey, "Surgery of the Heart," Chapter 20, (1955) pp. 686-737.

Bernal et al., "The 'Valve Racket': a new and different concept of atrioventricular valve repair," Eur. J. Cardio—thoracic Surgery 29:1026-29 (2006).

Bhudia, #58 Edge-to-edge mitral repair: a versatile mitral repair technique, 2003 STS Presentation, [Abstract Only].

Bhudia et al., "Edge-to-edge (Alfieri) mitral repair: results in diverse clinical settings," Ann Thorac Surg, 77: 1598-1606, (2004).

Bollling et al., "Surgery for acquired heart disease," (1995) 109:676-683.

Borghetti et al., "Preliminary observations on haemodynamics during physiological stress conditions following 'double-orifice' mitral valve repair," European Journal of Cardio-thoracic Surgery, Apr. 18, 2001 20:262-269.

Castedo, "Edge-to-edge tricuspid repair for redeveloped valve incompetence after DeVega's annuloplasty," AnnThora Surg, (2003) 75;605-6.

Dec et al., "Idiopathic dilated cardiomyopathy," N. Engl. J. Med., (1994) 331:1564-1575.

Dottori et al., "Echocardiographic imaging of the Alfieri type mitral valve repair," Ital Heart J, (2001) 2(4):319-320.

Downing et al., "Beating heart mitral valve surgery: Preliminary model and methodology," Journal of Thoracic and Cardiovascular Surgery, (2002) 123(6):1141-1146.

Falk et al., "Computer-enhanced mitral valve surgery: toward a total endoscopic procedure," Seminars in thoracic and cardiovascular surgery, (1999) 11(3):224-249.

Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).

Frazier et al., #62 Early Clinical Experience With an Implantable, Intracardiac Circulatory Support Device: Operative Considerations and Physiologic Implications, 2003 STS Presentation, 1 page total. [Abstract Only].

Fucci et al., "Improved results with mitral valve repair using new surgical techniques" Eur. J. Cardiothorac Sug. (1995) 9:621-627 (Medline Record enclosed herewith.).

Fundaro et al., "Chordal plication and free edge remodeling for mitral anterior leaflet prolapse repair: 8-year follow-up," Annals of Thoracic Surgery, (2001) 72:1515-1519.

Garcia-Rinaldi et al., "Left ventricular volume reduction and reconstruction is ischemic cardiomyopathy," Journal of Cardiac Surgery, (1999) 14:199-210.

Gateliene, "Early and postoperative results of metal and tricuspid valve insufficiency surgical treatment using edge-to-edge central coaptation procedure," (2002) 38 Suppl 2:172-5.

Gatti et al., "The edge to edge technique as a trick to rescue an imperfect mitral valve repair," Eur J Cardiothorac Surg, (2002) 22(5):817 20.

Gillinov et al., "Is minimally invasive heart valve surgery a paradigm for the future?," Current Cardiology Reports, (1999) 1:318-322.

Gundry, "Facile mitral valve repair utilizing leaflet edge approximation: midterm results of the Alfieri figure of eight repair," Presented at the Meeting of the Western Thoracic Surgical Association, (1999).

Gupta et al., #61 Influence of Older Donor Grafts on Heart Transplant Survival: Lack of Recipient Effects, 2003 STS Presentation, [Abstract Only].

Ikeda et al., "Batista's operation with coronary artery bypass grafting and mitral valve plasty for ischemic dilated cardiomyopathy," the Japanese Journal of Thoracic and Cardiovascular Surgery, (2000) 48:746-749.

Izzat et al., "Early experience with partial left ventriculectomy in the Asia-Pacific Region," Annuals of Thoracic Surgery, (1999) 67:1703-1707.

Källner et al., "Transaortic approach for the Alfieri Stitch," Ann Thorac Surg, 2001; 71:378-380.

Kameda et al., "Annuloplasty for severe mitral regurgitation due to dilated cardiomyopathy," Am. Thorac. Surg, (1996) 61:1829-1832.

Kavarna et al., "Transaortic repair of mitral regurgitation," Presented at the third annual New Era Cardiac Care conference, San Diego, CA, Jan. 13-16, 2000, http://www.hsforum.com/vol3/issue1/2000-2389print.html.

Kaza et al., "Ventricular reconstruction results in improved left ventricular function and amelioration of mitral insufficiency," Annals of Surgery, (2002) 235(6):828 832.

Khan et al., "Blade atrial septostomy: Experience with the first 50 procedures" Cathet. Cardiovasc. Diagn, (1991) 23:257-262.

Kherani et al., "Edge-to-edge mitral valve repair: the Columbia Presbyterian experience," Ann Thorac Surg, 2004; 78: 73-76.

Konertz et al., "Results after partial left ventriculectomy in a European heart failure population," J. Cardiac Surg, 1999; 14(2):129-135.

Kron et al., "Surgical relocation of the posterior papillary muscle in chronic ischemic mitral regurgitation," Annals. of Thoracic Surgery, (2002)74:600 601.

Krüger et al, "Edge to edge technique in complex mitral valve repair," Thorac Cardiovasc Surg, 2000, Thema: Poster, http://www.thieme.de/thoracic/abstracts/abstracts/p_73.html.

Langer et al., "Posterior mitral leaflet extensions: An adjunctive repair option for ischemic mitral regurgitation?, " J. Thorac. Cardiovasc. Surf. 131:868-77 (2006).

Lorusso e al., "Double-Orifice" technique to repair extensive mitral valve excision following acute endocarditis, J Card Surg, 1998; 13:24-26.

Lorusso et al., "The double-orifice technique for mitral valve construction: predictors of postoperative outcome," Eur J. Cardiothorac Surg, May 23, 2001; 20(3):583-589.

Maisano et al., "The double orifice repair for Barlow Disease: a simple solution for a complex repair," Supplement I Circulation, 1999; 100(18):1-94.

Maisano et al., "The double orifice technique as a standardized approach to treat mitral regurgitation due to severe myxomatous disease: surgical technique," Eur J. Cardiothoracic Surg., Jan 18, 2000; 17:201-215.

Maisano et al., "The hemodynamic effects of double-orifice valve repair for mitral regurgitation: a 3D computational model," European Journal of Cardio-thoracic Surgery, 1999; 15:419-425.

Maisano et al., "Valve repair for traumatic tricuspid regurgitation," Eur J. Cardio-Thorac Surg, 1996; 10:867-873.

Maisano et al., "The edge-to-edge technique: A simplified method to correct mitral insufficiency" Eur. J. Cardiothorac. Surg., (1998) 13:240-246.

Mantovani et al., "Edge-to-edge repair of congenital familiar tricuspid regurgitation: case report," J. Heart Valve Dis, Sep. 2000; 9 (5):641-643.

McCarthy et al. "Tricuspid valve repair with the Cosgrove-Edwards annuloplasty system" Am. Thorac. Surg., (1997) 64:267-268.

McCarthy et al., "Partial left ventriculectomy and mitral valve repair for end-stage congestive heart failure," Eur J. Cardio-thoracic Surgery, 1998; 13:337-343.

Moainie et al., Correction of traumatic tricuspid regurgitation using the double orifice technique, Annals of Thoracic Surgery, (2002) 73:963 965.

Morales et al., "Development of an off bypass mitral valve repair," The Heart Surgery Forum #1999-4963, (1999) 2(2):115-120.

Nakanishi et al., "Early outcome with the Alfieri mitral valve repair," J Cardiol, May 2001; 37(5):263-266, (Abstract in English; Article in Japanese.).

Nielsen et al., "The edge-to-edge mitral repair: tension on the approximating suture and leaflet deformation during acute ischemic mitral regurgitation in the ovine heart, " Circulation, 2001;104 [ suppl I]:I-29-I-35.

Noera et al.., "Tricuspid Valve Incompetence Caused by Nonpenetrating Thoracic Trauma", Annals of Thoracic Surgery, 1991, 51 (2), 320-322.

Osawa et al., "Partial left ventriculectomy in a 3 year old boy with dilated cardiomyopathy," Japanese Journal of Thoracic and Cardiovascular Surg, Sep. 2000, 48(9):590-593.

Park et al., "Clinical use of a blade atrial septostomy" Circulation (1978) 58:600-608.

Patel et al., #57 Epicardial Atrial Defibrillation: Novel Treatment of Postoperative Atrial Fibrillation, 2003 STS Presentation, [Abstract Only].

Privitera et al., "Mitral Valve Repair: Clinical Outcome and Pathology; Circulation," (2002) 106:173.

Redaelli et al., A computational study of the hemodynamics after 'edge-to-edge' mitral valve repair, Journal of Biomechanical Engineering, (2001) 123:565-570.

Reul et al., "Mital valve reconstruction for mitral insufficiency," Progress in Cardiovascular Diseases, (1997) vol. XXXIX, No. 6, pp. 567-599.

Ricchi et al., "Linear segmental annuloplasty for mitral valve repair" Ann. Thorac. Surg., (1997) 63:1805-1806.

Robicsek et al., #60 The Bicuspid Aortic Valve: How Does It Function? Why Does It Fail?, 2003 STS Presentation, [Abstract Only].

Tager et al., "Long-term follow-up of Rheumatic patients undergoing left-sided valve replacement with tricuspid annuloplasty—Validity of preoperative echocardiographic criteria in the decision to perform tricuspid annulopasty" Am. J. Cardiol., (1998) 81:1013-1016.

Tamura et al., Edge to edge repair for mitral regurgitation in a patient with chronic hemodialysis: report of a case, Kyobu Geka, (2001) 54(9):788-790.

Tibayan et al., #59 Annular Geometric Remodeling in Chronic Ischemic Mitral Regurgitation, 2003 STS Presentation, [Abstract Only].

Timek et al., "Edge-to-edge mitral repair: gradients and three-dimensional annular dynamics in vivo during inotropic stimulation," Eur J. of Cardiothoracic Surg., Jan. 9, 2001; 19:431-437.

Timek, "Edge-to-edge mitral valve repair without annuloplasty ring in acute ischemic mitral regurgitation," [Abstract] Clinical Science, Abstracts from Scientific Sessions, (2002) II-461.

Totaro et al., "Mitral valve repair for isolated prolapse of the anterior leaflet: an 11 year follow-up," Eur J. Cardio-Thoracic Surg, 1999; 15:119-126.

Uchida et al., "Percutaneous cardiomyotomy and valvultomy with angioscopic guidance," Am. Heart J., (1991) 121:1221-1224.

Umana et al., "'Bow-tie' mitral valve repair successfully addresses subvalvular dysfunction in ischemic mitral regurgitation," (1997) Surgical Forum pp. 279-280.

Umana, "'Bow-Tie' mitral valve repair: an adjuvant technique for ischemic mitral regurgitation," AnnThora Surg, (1998) 66:1640-6.

Votta et al., "3 D computational analysis of the stress distribution on the leaflets after edge to edge repair of mitral regurgitation," Journal of Heart Valve Disease, (2002)11:810 822.

European Search Report of EP Patent Application No. 04752714.8, dated May 7, 2010, 3 pages total.

* cited by examiner

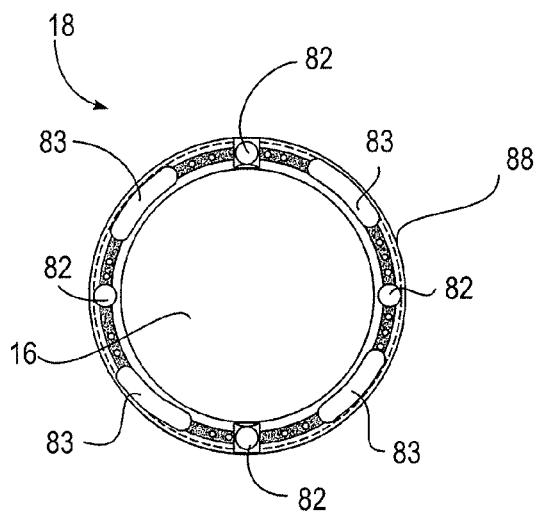
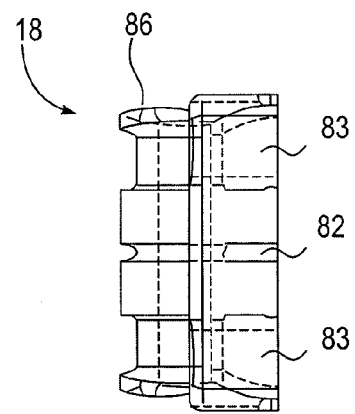
FIG. 10A  FIG. 10B
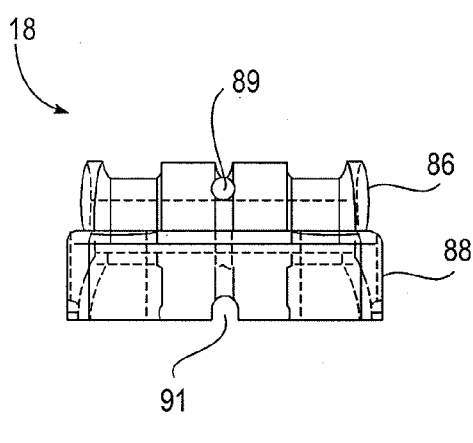
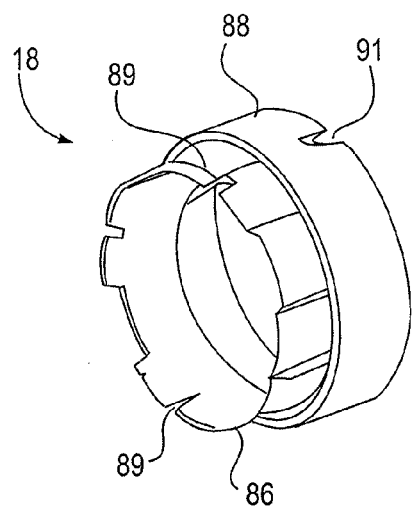
FIG. 10C  FIG. 10D

STEERABLE ACCESS SHEATH AND METHODS OF USE

CROSS-REFERENCES TO RELATED APPLICATIONS

This application is a continuation of U.S. patent application Ser. No. 12/392,670 filed Feb. 25, 2009 (now U.S. Pat. No. 7,682,319), which is a divisional of, and claims the benefit of priority from U.S. patent application Ser. No. 10/441,753 filed May 19, 2003 now abandoned, which is a continuation-in-part of, and claims the benefit of priority from U.S. patent application Ser. No. 09/894,463 filed Jun. 27, 2001 (now U.S. Pat. No. 6,752,813), which is a continuation-in-part of U.S. patent application Ser. No. 09/544,930 filed Apr. 7, 2000 (now U.S. Pat. No. 6,629,534), which is a non-provisional of, and claims the benefit of U.S. Provisional Application No. 60/128,690 filed on Apr. 9, 1999, the full disclosures of which are hereby incorporated herein by reference. This application is related to U.S. patent application Ser. Nos. 10/441,531 (now U.S. Pat. No. 7,563,267); Ser. No. 10/441,508; and Ser. No. 10/441,687 (now U.S. Pat. No. 7,226,467), the full disclosures of which are incorporated herein by reference.

BACKGROUND OF THE INVENTION

1. Field of the Invention

The present invention relates to an access sheath for endoluminally accessing a body cavity and directing the passage of interventional devices therethrough into the cavity. Particularly, the present invention relates to an articulatable access sheath which directs the interventional devices into the cavity in a desired orientation. In some embodiments, the present invention relates to vascularly accessing an atrium of the heart to direct an interventional catheter toward a cardiac valve.

To access a target location within the human body from a remote location, a catheter is typically passed through one or more body lumens, such as through the vascular system, to the target location. When the vascular system is used, a guidewire and dilator is inserted into an artery or vein through a relatively small incision in the patient's body. The guidewire and dilator is then threaded through the patient's vasculature to reach the desired target area. Often the dilator is covered by a sheath which is passed with the dilator to the target location. The dilator is then removed and the sheath is used as a conduit for access for a variety of medical devices to access the target location. Such devices may include catheters, surgical instruments, fiber optic cables for visualization, lasers, electronic devices, or sensors capable of monitoring physiological parameters in situ, to name a few. Although such access reduces the need for traditional invasive surgery, challenges arise related to control, manipulation, and positioning of instruments near the target location, particularly within a target body cavity.

A device advanced to the cavity will typically protrude into the cavity at the angle in which it entered. If the target tissue is not within this pathway, the device will need to be steered toward the target tissue. If more than one device is used during a procedure, each device will need to be steered and repositioned when used. This increases the time and cost of the procedure and also the risk of misalignment.

For example, to gain access to the left atrium of the heart, the catheter and/or access sheath may be tracked from a puncture in the femoral vein, through the inferior vena cava, into the right atrium and through a puncture in the intra-atrial septum to the left atrium. This pathway may then be used to access the mitral valve which lies between the left atrium and the left ventricle. From the point of entry through the septum, the mitral valve may be located below and to the right or left requiring the devices which are inserted to be directed downward and perhaps laterally after entry, toward the mitral valve. In addition, devices used for applying interventional therapies to the mitral valve may require precise alignment with the valve commissures, leaflets, or coaptation line to perform the procedure. When such procedures require the use of more than one instrument, each instrument would be dependent upon proper positioning in relation to the valve. This would require that positioning or steering mechanisms be built into each instrument and each instrument would be required to be properly positioned when introduced. This adds cost, complexity, and time to the overall procedure.

To overcome some of these challenges, access sheaths have been developed to direct instruments that are passed therethrough. For example, an access sheath having a pre-shaped curve at its distal end has been developed to both assist in negotiating twists and branches common in a patient's arterial or venous system and to maintain a shape once positioned within a target cavity. Since the pre-shaped curve is fixed into the access sheath at the time of manufacture, the radius and extent of the curvature generally cannot be altered. Due to anatomical variations, extensive pre-surgical planning would be necessary to determine the correct curvature of the access sheath. Such tailoring would be prohibitively complex and a predicted curvature would most likely still require additional repositioning once inside the body. Continuously replacing the pre-shaped access catheter in hopes of obtaining the proper curvature would be expensive and time consuming, possibly placing the patient at additional risk.

Steerable guide catheters and delivery catheters have been developed to more effectively navigate through the tortuous pathways of some body lumens, particularly the vascular system. Typically steering is accomplished through a combination of torqueing the proximal end of the catheter and pulling various pullwires to deflect the distal end of the catheter. Unfortunately, torque transmission has not been perfected in such steerable catheters. Due to the length of the catheter body between a proximal control end and the distal tip, torsion can tend to accumulate as the proximal end of the catheter is twisted to rotate the tip. The accumulated torsional moment may release unevenly, resulting in skipping or rapid rotation of the distal tip inside the vessel. To optimize torque transmission, the walls of such steerable catheters generally comprise a series of layers. In a typical steerable catheter, a woven metal or polymeric tubular braid may be sandwiched between an inner tubular sleeve and an outer tubular jacket. As a consequence, improved torquability generally results in increased wall thickness, which in turn increases the outside diameter of the steerable catheter or reduces any given desired inside diameter. In addition, such a heavy braided construction is often difficult to deflect by actuation of pullwires. To overcome this, the deflectable section can be softened with coils or softer polymers to allow it to be deflected to a much greater extent. However, this reduces the catheter's ability to transmit torque to or through this softer section. In addition, these softer sections may not offer adequate support for interventional devices or tools which are later passed through its inner lumen.

For these reasons, it would be desirable to provide an access sheath having an articulatable distal end which does not rely on permanent pre-shaping or torque transmission for positioning the access sheath within a target body cavity in a desired orientation. The articulatable access sheath should have a large lumen diameter to accommodate the passage of a variety of interventional devices, should have good wall strength to avoid kinking or collapse of the sheath when bent around tight curves, and should have good column and tensile strength to avoid deformation when the interventional devices are passed through the lumen. The sheath articulation mechanisms should provide for a high degree of controlled deflection at the distal end of the sheath but should not take up significant lumen area to allow for passage of interventional devices. Further, the access sheath should be articulatable in a manner which allows compound curves to be formed, for example curvature within more than one plane. Such manipulation should allow fine control over the distal end to accommodate anatomical variations within the same type of body cavity and for use in different types of body cavities.

2. Description of the Background Art

Hermann et al. (U.S. Pat. No. 5,843,031) describes a large-diameter introducer sheath having a hemostasis valve and a removable steering mechanism. The steering mechanism is described to be within an obturator which is positioned within the sheath during positioning and is then removable. Adair (U.S. Pat. No. 5,325,845) describes a steerable sheath having an articulatable member which is deformable to allow articulation. Kordis (U.S. Pat. No. 5,636,634) describes a sheath which is positioned by a separate, dedicated steering catheter.

A number of the other references refer to guidewires or catheters which themselves are steerable by means of wires. For example, Stevens-Wright et al. (U.S. Pat. No. 5,462,527) describes a handle which applies tension selectively to two or four pull cables to steer an attached catheter. Stevens-Wright et al. (U.S. Pat. No. 5,715,817) further describes improvements in actuating the tip of the catheter described in Stevens-Wright et al. '527.

Hammerslag (U.S. Pat. No. 5,108,368) describes a steerable guidewire or catheter wherein the tip is deflectable through a full 360 degree range of motion by means of axially moveable deflection wires extending throughout. Hammerslag (U.S. Pat. No. 5,820,592) describes a guide catheter through which a torque control wire or a deflection wire extends. Manipulating an actuator controls the wire to steer or aim the guide catheter. Savage (U.S. Pat. No. 5,368,564) and Savage et al. (U.S. Pat. No. 5,507,725) also describe a steerable catheter having wire members extending through the catheter wall to manipulate the tip.

Likewise, the following also provide variations of the steerable catheters which utilize wires for manipulation: Accisano, III (U.S. Pat. No. 5,571,085), Krauter (U.S. Pat. No. 5,359,994), West et al. (U.S. Pat. No. 5,318,525), Nardeo (Pub. No. US 2001/0037084 A1), Bumbalough (U.S. Pat. No. 6,267,746), Webster, Jr. (U.S. Pat. No. 6,123,699), Lundquist et al. (U.S. Pat. No. 5,195,968) and Lundquist et al. (U.S. Pat. No. 6,033,378). Falwell et al. (U.S. Pat. No. 6,319,250) describes a catheter having any suitable steering mechanism known in the art.

BRIEF SUMMARY OF THE INVENTION

The present invention provides devices, systems, methods and kits for endoscopically accessing a body cavity and providing a directed pathway toward a target tissue within the cavity. The directed pathway is provided by an access sheath which is positioned in a desired configuration, generally directed toward the target tissue. Interventional devices may then be passed through the sheath to the target tissue. Depending on the location of the target tissue and the desired angle of approach, the access sheath may be required to maintain one or more curves in one or more planes to properly direct the interventional devices. The access sheath of the present invention has a portion which comprises a series of articulating members to allow the sheath to form these curvatures. In addition, the access sheath has a locking feature to hold the articulating members in place and maintain the desired configuration. The articulating members may be positioned by an articulating mechanism within the sheath, such as pullwires which extend through at least one of the articulating members. Or, an articulatable obturator may be positioned within the sheath, wherein articulation of the obturator in turn moves the encasing sheath into the desired articulated position. The obturator is then removed and the sheath remains in the articulated position. Thus, the present invention allows the target tissue to be repeatedly accessed through the access sheath without the need to incorporate steering mechanisms into each interventional device or the need to spend additional time repositioning each interventional device upon use.

In a first aspect of the present invention, an articulatable access sheath is provided for accessing the body cavity. The access sheath comprises a shaft having a proximal end, a distal end and a central lumen therethrough. The distal end is sized appropriately for the intended method of approaching the body cavity. The body cavity may be approached laparoscopically, thorascopically, endoscopically, endovascularly, percutaneously or by any suitable method. Preferably, the distal end of the access sheath is passable through a body lumen, such as a blood vessel within the vascular system. This is particularly the case when approaching a chamber of the heart, which can be accessed either through the femoral vein and inferior vena cava or the superior vena cava into the right atrium, or through a femoral or axillary artery and the aorta into the left ventricle. The distal end may further be configured to penetrate the interatrial septum so as to be passed from the right atrium to the left atrium. Other body lumens through which the device may be positioned include the esophagus for approaching the stomach, the colon for approaching the gastrointestinal system, the trachea for approaching the lungs, or the urethra for approaching the urinary tract. In other instances, the distal end of the access sheath is passable directly through body tissues, such as in a direct access procedure to the heart. The access sheath may be positioned in a penetration in the chest wall and used to access the outside of the heart to perform diagnostic and interventional procedures such as ablation of the pulmonary veins to treat atrial fibrillation. Alternatively, the sheath may be passed through the wall of the heart to access the interior chambers thereof. The central lumen extends through the length of the shaft and is sized for passage of an interventional device, such as a catheter or tool, to perform procedures such as valve repair, electrophysiological mapping and ablation, and septal defect repair. To accommodate a variety of interventional devices, the central lumen is generally relatively large in comparison to the total cross section of the shaft.

The shaft also includes a portion which comprises a series of articulating members. The articulating members may have any suitable shape, however in preferred embodiments the members comprise interfitting domed rings. The ring aspect provides a hollow interior which forms the central lumen. The dome aspect provides a surface which is rotatable against an interfitting surface of an adjacent domed ring. Since the domed rings are individually rotatable, the series of articulating members can be positioned in a variety of arrangements to follow any pathway. Typically, the portion of the shaft comprising the series of articulating members is the distal end. This is because the distal end is usually advanced into the body cavity and benefits from articulation to properly direct interventional devices which are passed through. However, it may be appreciated that the articulating portion may be disposed at any location along the shaft and more than one portion having a series of articulating members may be present.

In some embodiments, the sheath includes at least one pullwire to articulate the articulating members. The pullwires extend through at least one of the articulating members to move the portion of the shaft having the articulating members into an articulated position. The pullwires can extend through the central lumen or through individual lumens in the walls of the articulating members. It may be appreciated that more than one pullwire may extend through any given lumen. To provide optimal positioning of the shaft, a plurality of pullwires are present at locations around the perimeter of the central lumen. The presence of each pullwire allows articulation of the shaft in the direction of the pullwire. For example, when pulling or applying tension to a pullwire extending along one side of the shaft, the shaft will bend, arc or form a curvature toward that side. To then straighten the shaft, the tension may be relieved for recoiling effects or tension may be applied to a pullwire extending along the opposite side of the shaft. Therefore, pullwires can be symmetrically placed along the sides of the shaft. Although any number of pullwires are possible, generally, four to eight pullwires are preferred.

Each pullwire is attached to the shaft at a location chosen to result in particular curvature of the shaft when tension is applied to the pullwire. For example, if a pullwire is attached to the most distal articulating member in the series, applying tension to the pullwire will compress the articulating members proximal to the attachment point along the path of the pullwire. This results in a curvature forming in the direction of the pullwire proximal to the attachment point. It may be appreciated that the pullwires may be attached to any location along the shaft and is not limited to attachment to articulating members.

When more than one curvature is desired, pullwires are attached at various attachment points, each attachment point providing a different curvature or altering the overall articulated position of the sheath. For example, when a first pullwire is fixedly attached to the shaft at a primary attachment point, applying tension to the first pullwire arcs the series of articulating members proximal to the primary attachment point to form a primary curve. If the distal end terminates in a distal tip and the primary attachment point is located at the distal tip, the primary curve will extend through the entire series of articulating members. If the primary attachment point is located mid-way along the series of articulating members, the primary curve will extend through the series of articulating members proximal to the primary attachment point. When a second pullwire is fixedly attached to the shaft at a secondary attachment point, applying tension to the second pullwire arcs the series of articulating members proximal to the secondary attachment point to form a secondary curve. The primary and secondary curves may lie in the same plane or in different planes. In some embodiments, the planes are substantially orthogonal.

In some embodiments, a third pullwire is fixedly attached to the shaft at a distal attachment point and applying tension to the third pullwire moves the distal end through an angle theta. In particular, when the distal attachment point is located near the distal tip, the third pullwire moves the distal tip through the angle theta. The angle theta will be described and illustrated in more detail in later sections. However, the angle theta generally serves to tip or angle the distal tip in relation to a center line to further refine the articulated position of the sheath. Often the angle theta lies in a plane which is different from at least the primary curve or the secondary curve and sometimes both. In fact, the angle theta may lie in a plane which is orthogonal to both the primary curve and the secondary curve.

Tension is applied to the pullwires by manipulation of actuators located on a handle. The handle is connected with the proximal end of the articulatable access sheath and remains outside of the body. The actuators may have any suitable form, including buttons, levers, knobs, switches, toggles, dials, or thumbwheels, to name a few. Each actuator may apply tension to an individual pullwire or to a set of pullwires, or may actuate the articulation element according to its type. Generally, a different actuator is used to form each curvature, such as the primary curvature and secondary curvature, and to cause movement through the angle theta. The handle may also include a locking actuator to actuate a locking mechanism.

Locking holds the articulating members in the articulated position. By such locking, the sheath is maintained in the articulated position while interventional devices are passed therethrough. The sheath will retain sufficient rigidity to deflect and guide a non-steerable interventional device through its central lumen and direct the device to the body cavity, particularly to the target tissue within the body cavity. In some embodiments, the locking feature comprises sufficient friction between articulating members so that the members are held in place, either by friction of one articulating member against another or by the presence of frictional elements between the articulating members. In other embodiments, the locking feature comprises a locking mechanism which includes a mechanism for holding at least one of the pullwires in the tensioned position. As described previously, tensioning of a pullwire typically draws a portion of the articulating members together, forming a curve. By holding the pullwire in this tensioned position, the articulated members can often maintain this arrangement. By holding more pullwires in place, the ability to maintain the arrangement is increased. Therefore, some locking mechanisms will hold all of the pullwires in a tensioned position. When individual pullwires control individual portions of the series of articulated members, the portions may be individually locked by holding tension in the appropriate pullwires. This may be useful, for example, when a desired primary curve is established and a secondary curve is undertaken. The primary curve may be locked in place prior to creating the secondary curve to allow independent creation of each curve.

Although only a few types of curves have been described in relation to the articulated position, it may be appreciated that any number of curves or shapes may be formed throughout the series of articulating members. In addition, permanent curves may also be provided throughout the portion of the shaft comprising the series of articulating members. Such permanent curves may be a result of the shapes of the articulating members, the way in which the articulating members are arranged or fit together, or of any other mechanism. Further, any number of curves or shapes may be pre-formed throughout portions of the shaft other than the portion of the shaft comprising the series of articulating members. And, alternative articulation elements may also be used, such as pushrods, thermally-controlled shape memory alloy wires, or hydraulic or pneumatic fluids, to name a few.

In a second aspect of the present invention, an access system for accessing a body cavity is provided. The access system comprises a sheath which includes a shaft having a proximal end, a distal end and a central lumen therethrough. Again, the distal end is sized appropriately for the intended method of approaching the body cavity. And, a portion of the shaft comprises a series of articulating members which are lockable in a fixed position. The access system further comprises an obturator sized for passage through the central lumen and having means for articulating the obturator. Articulation of the obturator positions the articulating members of the sheath in an articulated position which becomes the fixed position upon locking. The obturator is then removed so that interventional devices may be passed therethrough.

The portion of the shaft comprising the series of articulating members may be the same or similar to that described above in relation to the articulatable access sheath. Again, in preferred embodiments the articulating members comprise interfitting domed rings, each domed ring independently rotatable against an adjacent domed ring. And, pullwires may be present which pass through the at least one of the articulating members. However, in this embodiment, the pullwires are not used to position the articulating members, rather the pullwires are used to lock the articulating members in the fixed position. In some embodiments, the pullwires hold the articulating members in contact with enough frictional force to hold or lock the articulating members in the fixed position. In other embodiments, tension may be applied to some or all of the pullwires to further wedge the articulating members together and therefore lock them in place.

The articulating members are moved into the articulated position by action of the obturator. Once the obturator has been placed within the central lumen of the shaft, the obturator can be moved into any arrangement. For example, the obturator may be shaped to have bends, arcs, curves or angles. Such shaping can be achieved by any suitable mechanism, including pullwires which act similarly to those described above in relation to articulating the articulatable access sheath. The shaping of the obturator applies forces to the central lumen and transfers the shaping to the surrounding sheath. Again, the articulated position can include any number of curves, including a primary curve, secondary curve or angle theta, to name a few. And, the curves may lie in the same or different planes.

Articulation of the obturator can be achieved by manipulation of actuators located on an obturator handle. The obturator handle is connected with the proximal end of the obturator and remains outside of the body. Again, the actuators may have any suitable form, including buttons, knobs, switches, toggles, dials, or thumbwheels, to name a few. Each actuator may apply tension to an individual pullwire or to a set of pullwires. Generally, a different actuator is used to form each curvature, such as the primary curvature and secondary curvature, and to cause movement through the angle theta. The obturator handle may also include an obturator locking actuator to actuate an obturator locking mechanism.

The obturator locking mechanism locks the obturator in the articulated position. By such locking, the obturator is maintained in the articulated position while the sheath is then locked in position. In some embodiments, the locking mechanism of both the obturator and sheath include a mechanism for holding at least one of the pullwires in the tensioned position. Some locking mechanisms will hold all of the pullwires in a tensioned position. When individual pullwires affect individual portions of the obturator or the series of articulated members, the portions may be individually locked by holding tension in the appropriate pullwires.

Again, although only a few types of curves have been described in relation to the articulated position, it may be appreciated that any number of curves or shapes may be formed throughout the obturator. In addition, permanent curves may also be pre-set throughout obturator, such as by heat-setting. These permanent curves will then also be transferred to the surrounding sheath.

After the sheath has been locked in place, the obturator can then be unlocked and removed. Or, when the obturator has a permanent heat-set curve, the locked sheath will be sufficiently rigid enough to allow removal of the pre-curved obturator without changing the shape of the sheath. The sheath will also retain sufficient rigidity to deflect and guide a non-steerable interventional device through its central lumen and direct the device to the body cavity, particularly to the target tissue within the body cavity.

In other embodiments, the obturator may only form a single curve yet may be used to form compound or multiple curves in the sheath. For example, the obturator may be positioned in a first location along the sheath forming a first curve. The sheath is then locked in place in this first location to hold the first curve. The obturator may then be positioned in a second location along the sheath forming a second curve. Likewise, the sheath is then locked in the second location to hold the second curve. Hence, multiple or compound curves may be formed from an obturator capable of forming a single curve. This concept may be extrapolated to cover obturators capable of forming more than a single curve yet are used to form curves in sheath which are more complex or of a higher number.

In a third aspect of the present invention, methods of accessing a body cavity are provided. In one embodiment, the method includes advancing a sheath through a body lumen to the body cavity, wherein the sheath includes a shaft having a proximal end, a distal end, a central lumen therethrough, and a portion of the shaft comprises a series of articulating members. Although the sheath can be used to access any body cavity through any pathway, such as laparoscopically, thorascopically, endoscopically, endovascularly or percutaneously, the sheath may particularly be used to access one or more chambers of the heart. The chambers of the heart provide access to many tissues which may be targeted for treatment, such as valves, chordae tendinae, papillary muscles, the Purkinje system, pulmonary veins and coronary arteries, to name a few. When targeting the mitral valve, the left atrium may be accessed to approach the valve from above. To accomplish this, the sheath may be advanced through the vasculature to the right atrium and passed through the intra-atrial septum to the left atrium. The articulating members are then articulated to move the portion of the shaft comprising the series of articulating members into an articulated position. It may be appreciated that the mitral valve may alternatively be approached from below or from the ventricular side by accessing the left ventricle. This is typically achieved by advancing the sheath through the vasculature to the aorta, through the aortic valve and into the left ventricle. Examples of this approach and other approach methods are provided in U.S. patent application Ser. No. 09/894,463 filed on Jun. 27, 2001 incorporated by reference herein for all purposes. In a further alternative approach, the access sheath may be positioned through a surgical penetration in the chest wall and through a penetration in a wall of the heart to access the cardiac chambers. Preferably, for mitral valve and other procedures in the left side of the heart, the access sheath is introduced into the right atrium and then advanced across the interatrial septum into the left atrium.

As described previously, the articulated position may include any number of curves or shapes to properly direct the sheath toward the target tissue. When targeting the mitral valve via the right atrium, the distal end of the sheath extends into the open space of the right atrium. To direct the distal tip of the sheath toward the mitral valve, the sheath may be articulated to move the distal tip laterally, vertically, or angularly, to name a few. For example, the articulated position may include a primary curve in a primary plane parallel to the valve surface. This moves the distal tip laterally in relation to the valve. The articulated position may further include a secondary curve in a secondary plane; typically the secondary plane is different from the primary plane and optionally substantially orthogonal to the primary plane. This moves the distal tip vertically and angularly, directing the central lumen toward or away from the valve along the secondary plane. In addition to these or additional curves, the articulated position may further include an angle theta. This moves the distal end vertically and angularly through a plane which differs from the secondary plane. Consequently, the central lumen can be directed toward or away from the valve along a theta plane which is different than the secondary plane and optionally the primary plane.

Articulating the articulating members may be accomplished by any of the means described above. For example, the sheath may further comprise at least one pullwire which extends through at least one of the articulating members. Applying tension to the at least one pullwire would thus articulate the articulating members. Once the articulating members are moved into a desired articulated position, the articulating members are locked in place. Locking the articulating members may comprise holding the tension in the at least one pullwire with a locking mechanism. As described previously, locking may be accomplished by holding tension in all of the pullwires.

Once the sheath is locked in the articulated position, interventional devices are then passed through the central lumen, wherein the articulated position directs the interventional device into the body cavity. In this example, an interventional catheter or tool is passed through the central lumen into the left atrium and directed toward the mitral valve. Depending on the direction provided by the sheath, the interventional device may optionally be advanced through the valve, between the leaflets. The desired surgical procedure can then be performed. If additional catheters or tools are needed, the devices may easily be interchanged by removing one and advancing another while the sheath remains in the articulated position.

In another embodiment, the method includes advancing a sheath through a body lumen to a body cavity, wherein the sheath comprises a shaft having a proximal end, a distal end, a central lumen therethrough and a portion of the shaft comprises a series of articulating members. However, in embodiment the method includes passing an obturator through the central lumen and articulating the obturator to position the articulating members in an articulated position. The obturator may be articulated by any of the means described previously. The articulated members are then locked in the articulated position and the obturator is removed to allow passage of an interventional device through the central lumen, wherein the articulated position directs the device into the body cavity.

In a fourth aspect of the present invention, the devices, systems and methods of the present invention may be provided in one or more kits for such use. The kits may comprise an access sheath and instructions for use. The access sheath may be articulatable by means of mechanisms incorporated in the sheath, or the kit may include an articulatable obturator for use in articulating the sheath. Optionally, such kits may further include any of the other system components described in relation to the present invention and any other materials or items relevant to the present invention.

Other objects and advantages of the present invention will become apparent from the detailed description to follow, together with the accompanying drawings.

BRIEF DESCRIPTION OF THE DRAWINGS

FIGS. 10A-E illustrate an embodiment of an articulating member which is designed to reduce possible binding of the pullwires and to increase stability of curves during articulation.

DETAILED DESCRIPTION OF THE INVENTION

Articulatable Access Sheath

Figure 1:
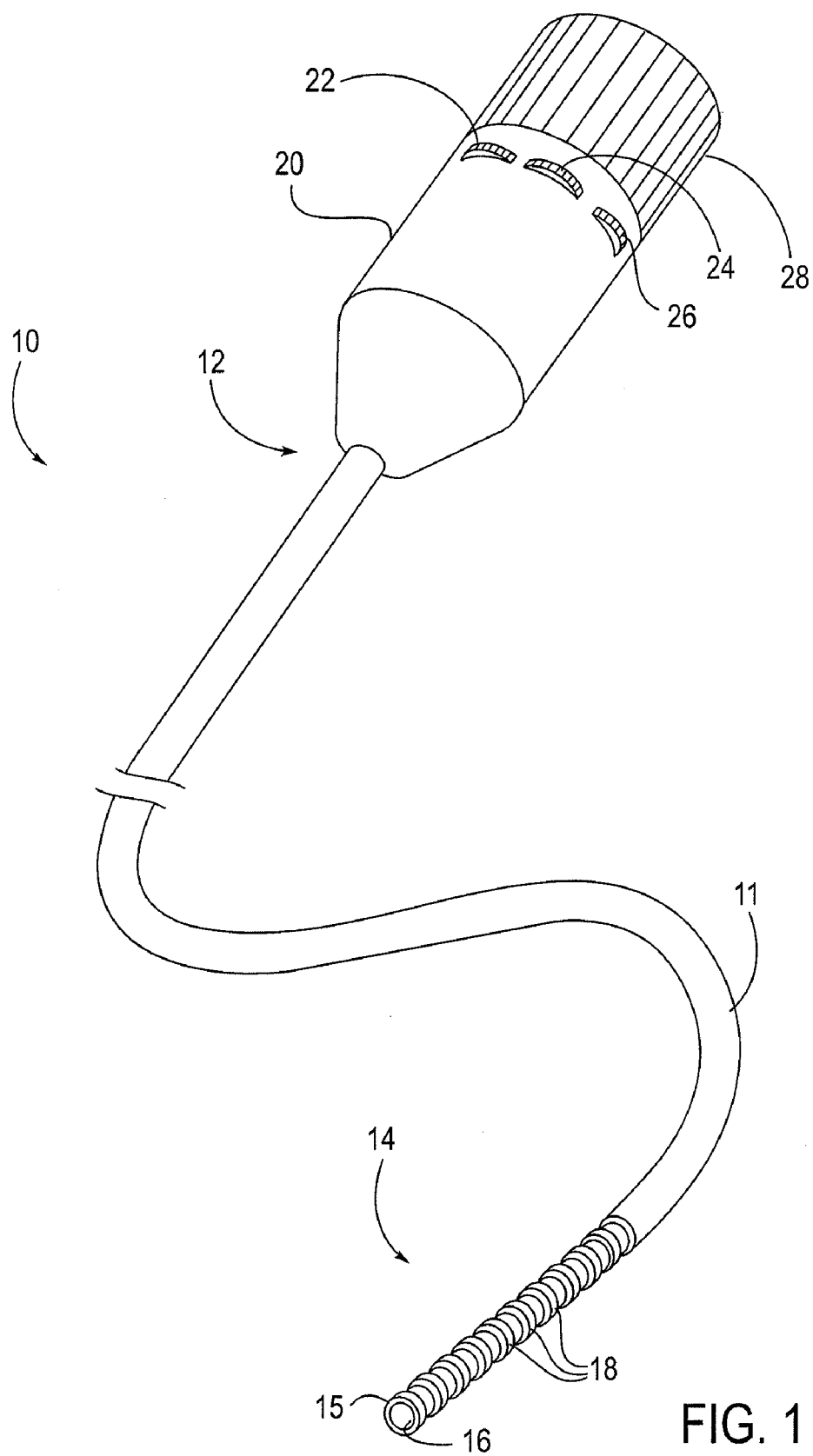
FIG. 1 is a perspective view of an embodiment of an articulatable access sheath of the present invention.

Referring to FIG. 1, an embodiment of an articulatable access sheath 10 of the present invention is illustrated. The sheath 10 comprises a shaft 11 having a proximal end 12, a distal end 14, and a central lumen 16 therethrough. The distal end 14 is sized to be passable through a body lumen to a body cavity. Therefore, the distal end 14 preferably has an outer diameter in the range of approximately 0.040 in. to 0.500 in., more preferably in the range of 0.130 in. to 0.300 in. The central lumen 16 is sized for passage of an interventional device therethrough. Therefore, the central lumen 16 preferably has an inner diameter in the range of approximately 0.030 in. to 0.450 in., more preferably in the range of 0.120 in. to 0.250 in. In addition, a portion of the shaft 11 is comprised of a series of articulating members 18. In this embodiment, the articulating members 18 are shown disposed at the distal end 14 of the shaft 11, terminating in a distal tip 15. Here, the articulating members 18 extend over the distal most 1 to 10 cm of the sheath 10. However, it may be appreciated that the articulating members 18 may be disposed at any location along the sheath. For example, if a straight or non-articulating portion is desired near the distal end 14, the articulating members 18 may be located at a more proximal position.

The portion of the shaft 11 having the articulating members 18 is movable into an articulated position by actuation of one or more positioning mechanisms. Actuation of the positioning mechanisms is achieved with the use of actuators, such as actuators 22, 24, 26 located on a handle 20. The handle 20 is connected to the proximal end 12 of the shaft 11 and remains outside of the patient's body during use. Actuators 22, 24, 26 are used to bend, arc or reshape the portion of the shaft 11 comprising articulating members 18. For example, a primary curve actuator 22 can be used to actuate one or more pull wires to form a primary curve in the portion of the shaft 11 comprising the series of articulating members 18. Further, a secondary curve actuator 24 can be actuated to form a secondary curve in the portion of the shaft 11 comprising the series of actuating members 18. And a theta actuator 26 can be manipulated to move the distal tip 15 through an angle theta. In addition, a locking actuator 28 may be used to actuate a locking mechanism to lock the articulating members 18 in the articulated position. Actuators 22, 24, 26, are illustrated as thumbwheels and actuator 28 is illustrated as a rotating knob. It may be appreciated that such actuators 22, 24, 26, 28 and any additional actuators located on the handle 20 may take any suitable form including knobs, buttons, levers, switches, toggles, sensors or other devices. In addition, the handle 20 may include a numerical or graphical display of information such as data indicating the articulated position of the sheath 10.

Example Articulated Positions

Figure 2A:
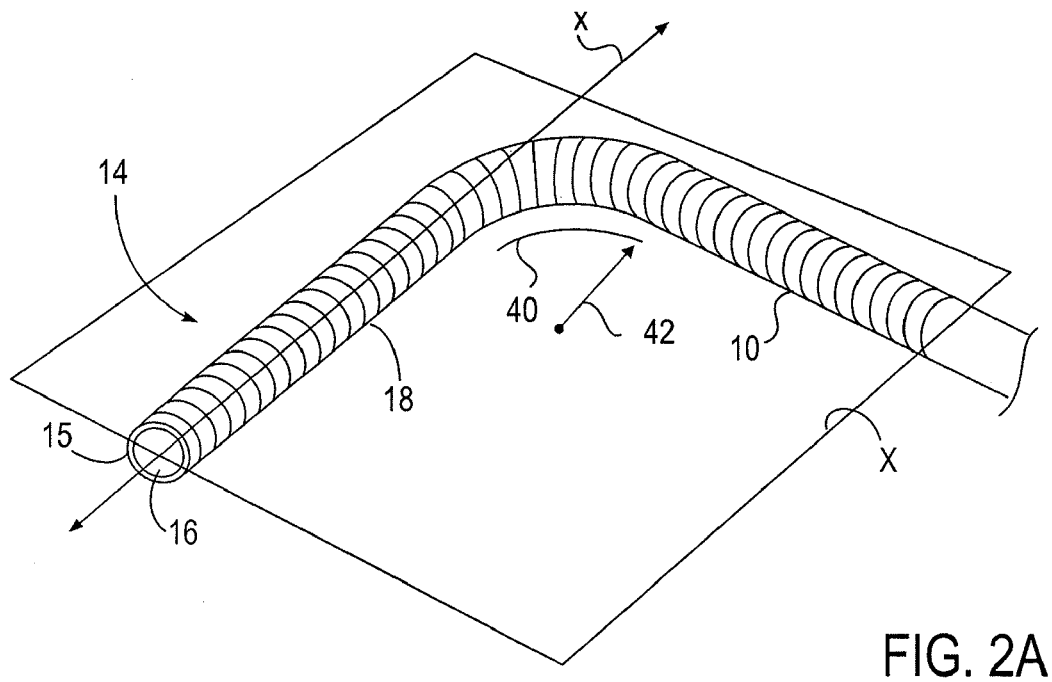
FIGS. 2A-2D illustrate examples of articulated positions of the access sheath.

FIGS. 2A-2D illustrate examples of articulated positions that the articulating members 18 of the access sheath 10 may hold. Referring to FIG. 2A, the articulating members 18 are configured to allow movement into an articulated position which includes a primary curve 40. The primary curve 40 typically has a radius of curvature 42 in the range of approximately 0.125 in. to 1.000 in., preferably in the range of approximately 0.250 in. to 0.500 in. As shown, when the articulated position includes only a primary curve 40, the articulating members 18 lie in a single plane X. An axis x, transversing through the center of the central lumen 16 at the distal tip 15, lies within plane X.

Figure 2B:
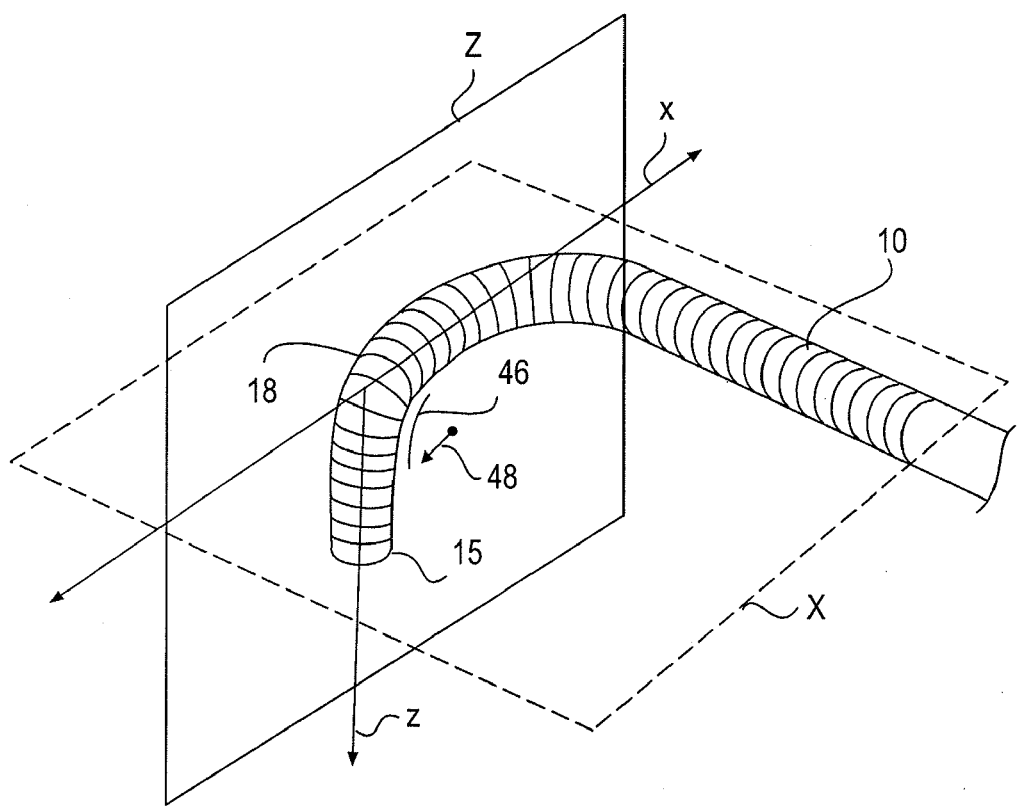

Referring to FIG. 2B, the articulating members 18 may further be configured to so that the articulated position further includes a secondary curve 46. The secondary curve 46 typically has a radius of curvature 48 in the range of approximately 0.050 in. to 0.750 in., preferably in the range of approximately 0.125 in. to 0.250 in. The secondary curve 46 can lie in the same plane as the primary curve 40, plane X, or it can lie in a different plane, such as plane Z as shown. In this example, plane Z is substantially orthogonal to plane X. Axis z, transversing through the center of the central lumen 16 at the distal tip 15, lies within plane Z. By comparing axis x to axis z, the movement of the distal tip 15 may be compared. Adjustment of the articulating members 18 to include the secondary curve 46 directs the central lumen 16 downward, as shown, along axis z. In this example, axis x and axis z are at substantially 90 degree angles to each other; however, it may be appreciated that axis x and axis z may be at any angle in relation to each other. Also, although in this example the primary curve 40 and the secondary curve 46 lie in different planes, particularly in substantially orthogonal planes, the curves 40, 46 may alternatively lie in the same plane.

Figure 2C:
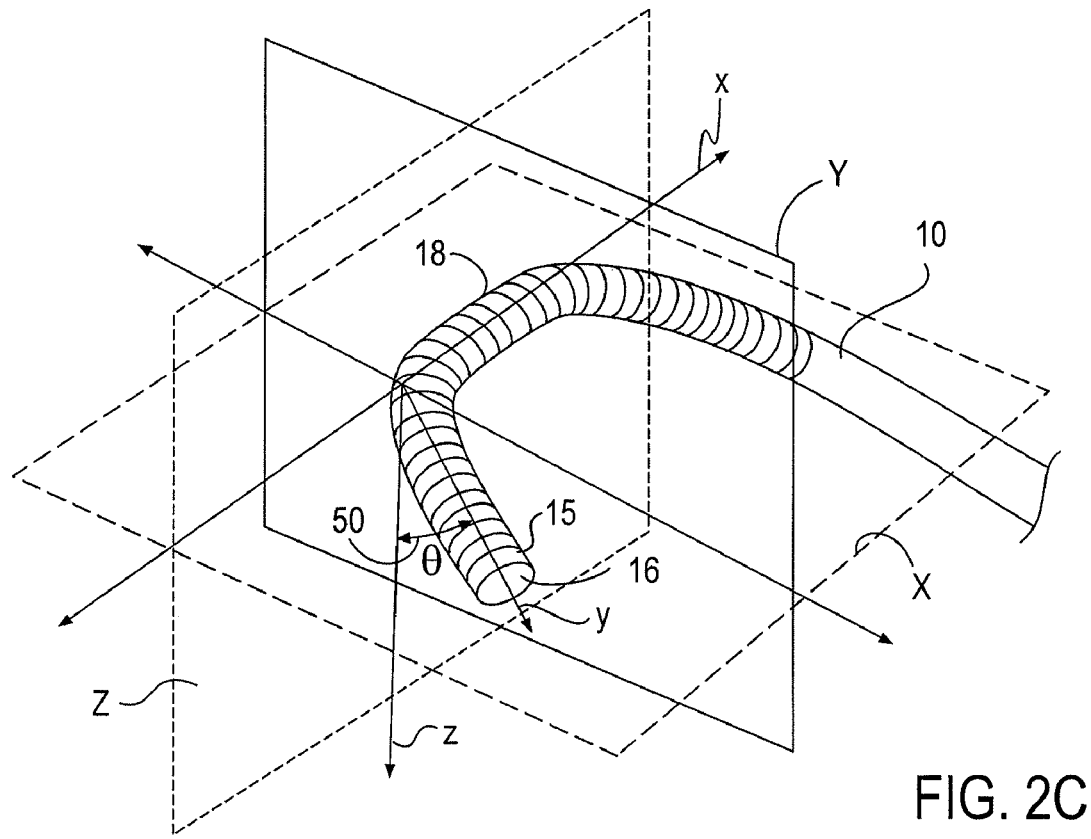

Referring now to FIG. 2C, the articulating members 18 may be further manipulated to allow the distal tip 15 to move through an angle theta 50. The angle theta 50 is in the range of approximately −100° to +100°, preferably in the range of approximately −50° to +50°. As shown, the angle theta 50 lies within a plane Y. In particular, axis y, which runs through the center of the central lumen 16 at the distal tip, forms the angle theta 50 with axis z. In this example, plane Y is orthogonal to both plane X and plane Z. Axes x, y, z all intercept at a point within the central lumen 16 which also coincides with the intersection of planes X, Y, Z.

Figure 2D:
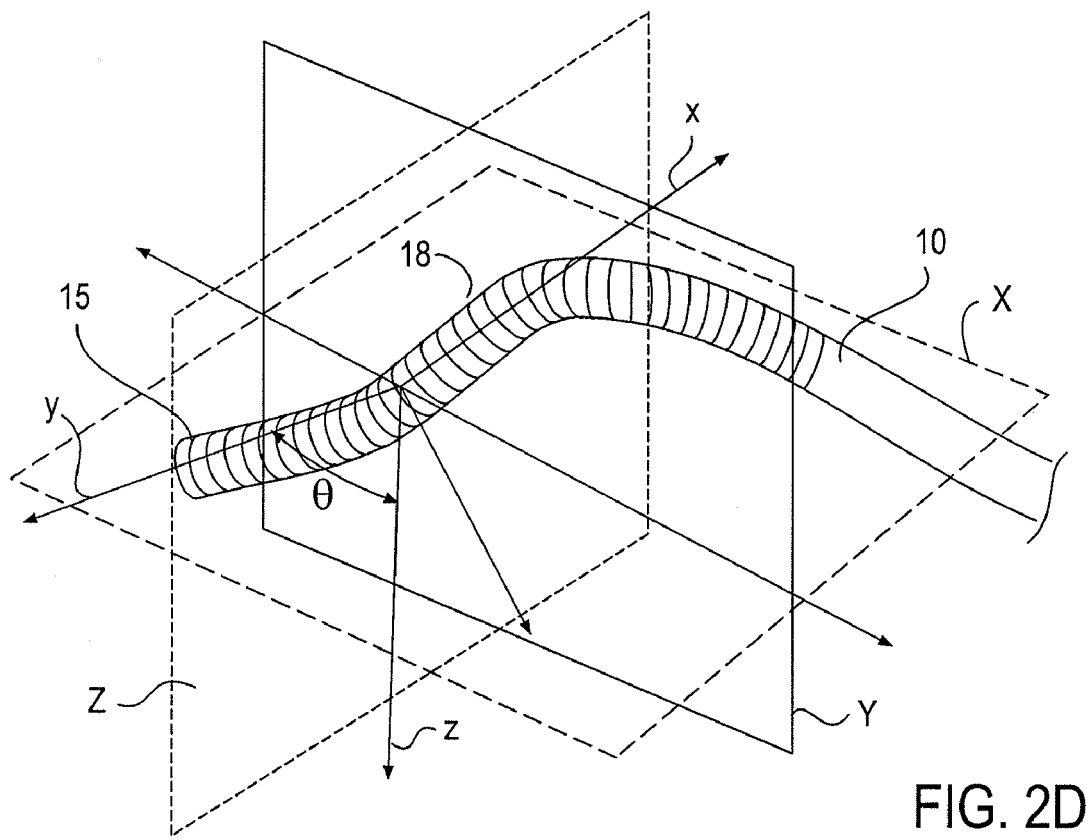

Similarly, FIG. 2D illustrates movement of the distal tip through an angle theta 50 on the opposite side of axis z. Again, the angle theta 50 is measured from the axis z to the axis y, which runs through the center of the central lumen 16 at the distal tip 15. As shown, the angle theta 50 lies in plane Y. Thus, the primary curve 40, secondary curve 46, and angle theta 50 can all lie in different planes, and optionally in orthogonal planes. However, it may be appreciated that the planes within which the primary curve 40, secondary curve 46 and angle theta 50 lie may be mutually dependent and therefore would allow the possibility that some of these lie within the same plane.

Figure 3:
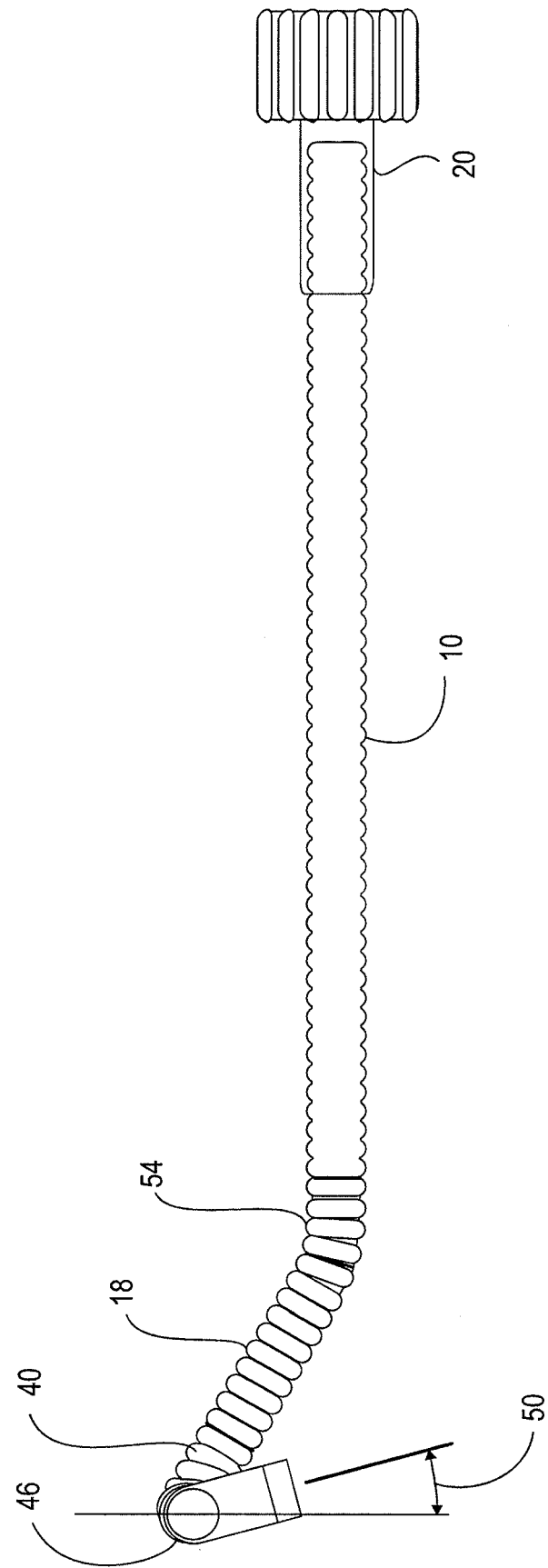
FIG. 3 is a perspective side view of an access sheath having an additional curve compared to the articulated positions shown in FIGS. 2A-2D.

Further, the articulating members 18 may be configured to provide additional curves or shapes. For example, as illustrated in FIG. 3, an additional curve 54 may be formed by the articulating members 18 proximal to the primary curve 40, secondary curve 46, and angle theta 50. Such additional curves 54 may be formed by the articulating members 18 by manipulation of the actuators on the handle 20, or the curves 54 may be permanently pre-formed. Likewise, any number of curves or shapes may be pre-formed throughout portions of the sheath other than the portion of the sheath comprising the series of articulating members 18. In addition or alternatively, pre-formed portions may be intermixed with the portion of the sheath comprising the series of articulating members 18, such as in an alternating pattern. Thus, any number of curves may be formed in the access sheath 10 to create the articulated position.

Figure 4A:
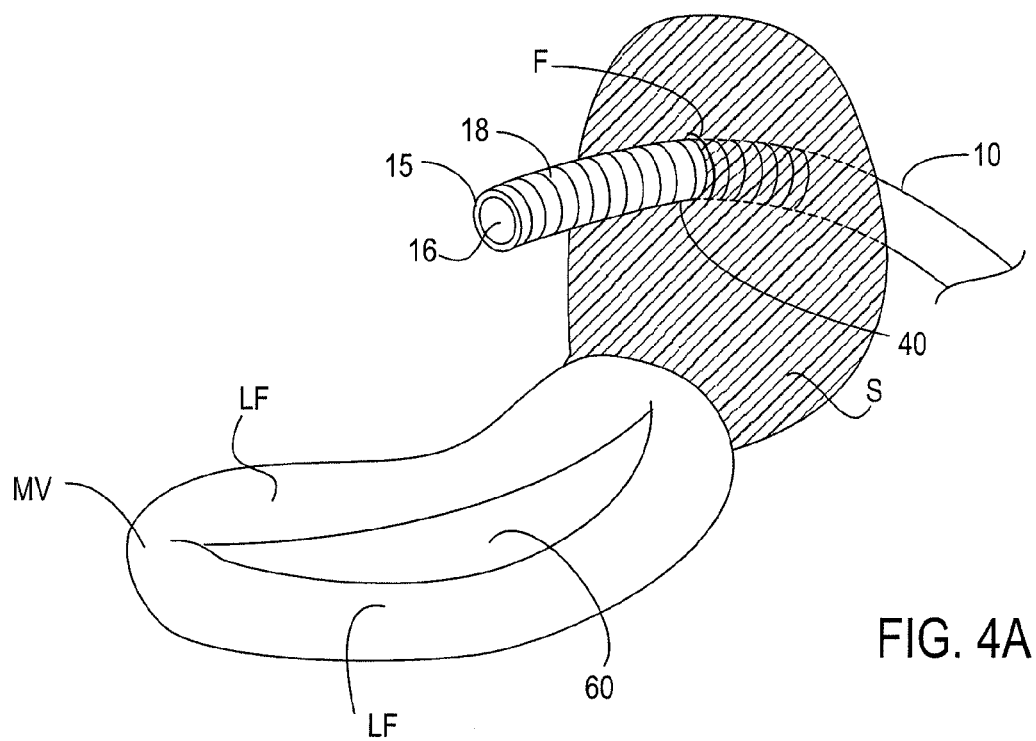
FIGS. 4A-4C illustrate a method of using the access sheath for accessing the mitral valve.
Figure 4B:
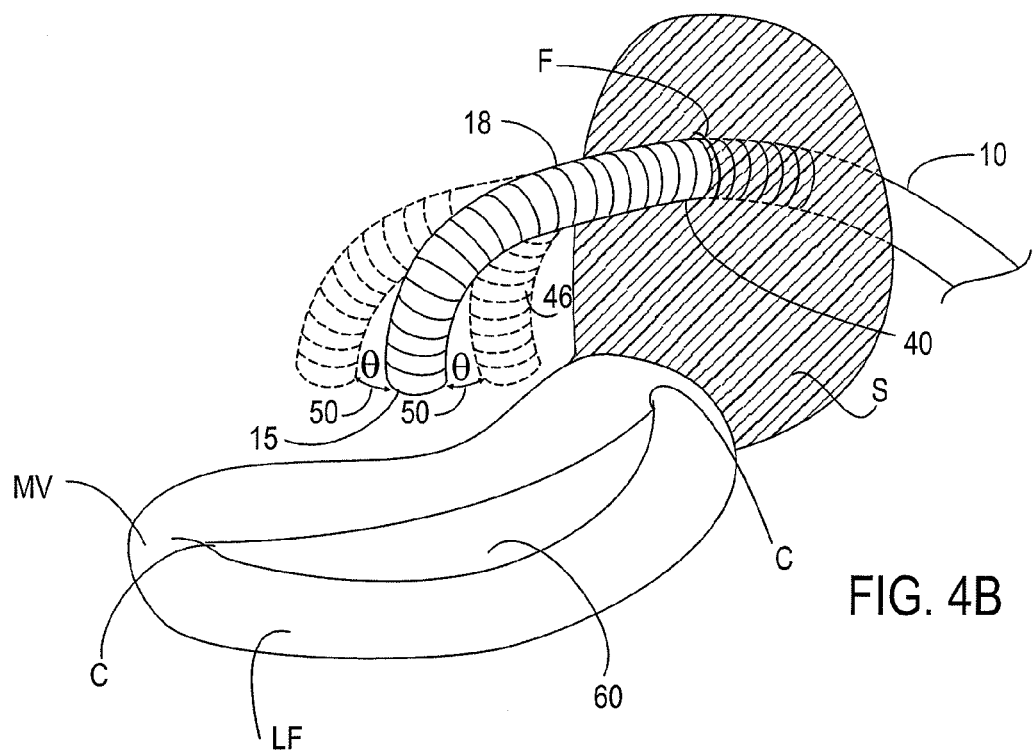
Figure 4C:
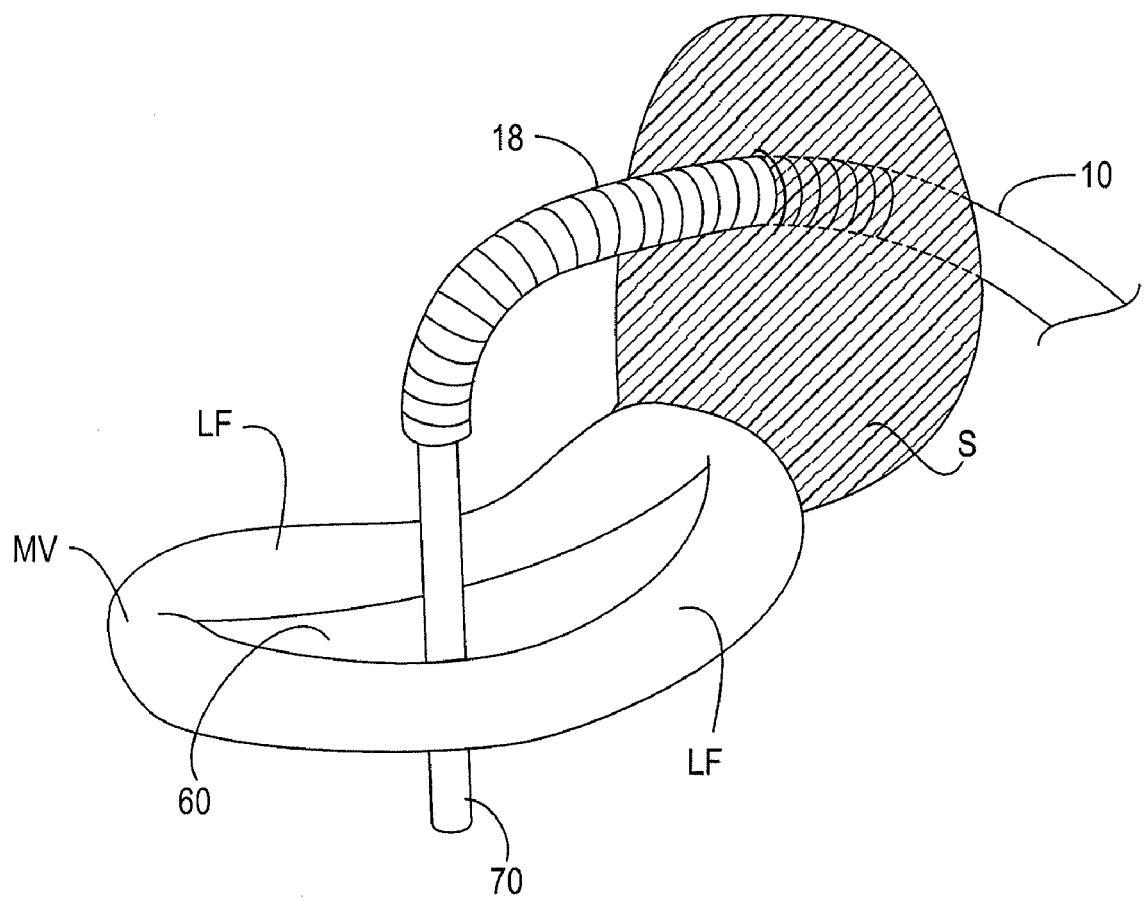

The articulated position of the access sheath 10 illustrated in FIGS. 2A-2D and FIG. 3 is particularly useful for accessing the mitral valve. FIGS. 4A-4C illustrate a method of using the access sheath 10 for accessing the mitral valve MV. To gain access to the mitral valve, the access sheath 10 may be tracked from a puncture in the femoral vein, through the interior vena cava and into the right atrium. As shown in FIG. 4A, the access sheath 10 may be punctured through a fossa F in the intra-atrial septum S. The access sheath 10 is then advanced through the fossa F so that the distal tip 15 is directed over the mitral valve MV. Again, it may be appreciated that this approach serves merely as an example and other approaches may be used, such as through the jugular vein, femoral artery, port access or direct access, to name a few.

It is then desired to move and tip the distal tip 15 so that the central lumen 16 is directed toward the target tissue, the mitral valve MV. In particular, the central lumen 16 is to be directed toward a specific area of the mitral valve MV, such as toward the opening 60 between the valve leaflets LF, so that a particular interventional procedure may be performed. A primary curve 40 may be formed by the series of articulating members 18, as described above. In this example, formation of the primary curve 40 moves the distal tip 15 within a primary plane, corresponding to previous plane X, parallel to the valve surface. This moves the distal tip 15 laterally along the short axis of the mitral valve MV, and allows the distal tip 15 to be centered over the opening 60. In this articulated position, any interventional devices which are passed through the central lumen 16 would be directed horizontally over the valve MV. To direct catheters or tools into the opening 60, it is necessary that the distal tip 15 is pointed downward towards the mitral valve MV.

Referring to FIG. 4B, the access sheath 10 is shown in an articulated position which includes a secondary curve 46 in a secondary plane, corresponding to previous plane Z. Formation of the secondary curve 46 moves the distal tip 15 vertically and angularly between the commissures C, directing the central lumen 16 toward the mitral valve MV. In this articulated position an interventional device which is passed through the central lumen 16 would be directed toward and/or through the opening 60. Although the primary curve 40 and the secondary curve 46 may be varied to accommodate different anatomical variations of the valve MV and different surgical procedures, further adjustment may be desired beyond these two curvatures for proper positioning of the access sheath 10.

Thus, the access sheath 10 may include additional curvatures throughout the articulating members 18 and/or include the ability of the distal tip 15 to move angularly through an angle theta 50. This moves the tip vertically and angularly through a theta plane, corresponding to previous plane Y. Movement of the distal tip 15 through the angle theta 50 in either direction is shown in dashed line in FIG. 4B. Consequently, the central lumen 16 can be directed toward the mitral valve MV within a plane which differs from the secondary plane. After such movements, the access sheath 10 will be in an articulated position which positions the distal tip 15 so that the opening of the central lumen 16 at the tip 15 faces the desired direction. Once the desired articulated position is achieved, the articulating members 18 are locked in place by a locking feature. The locking feature may simply be the articulating members holding the desired articulated position by friction during the articulation process. In this situation, the members are essentially already locked in place. The locking feature may alternatively be a locking mechanism which is activated, such as simultaneous tensioning of cables to compress the articulation members and locking of the cables in this tensioned position. In any case, such locking provides stiffness in the access sheath 10 for the passage of interventional devices 70, as illustrated in FIG. 4C. The interventional device 70 can be passed through the central lumen 16 toward the target tissue, in this case the mitral valve MV. Positioning of the distal end 15 over the opening 60, as described above, allows the device 70 to pass through the opening 60 between the leaflets LF if desired, as shown. At this point, any desired surgical procedure may be applied to the mitral valve for correction of regurgitation or any other disorder.

Articulating Members

Figure 5:
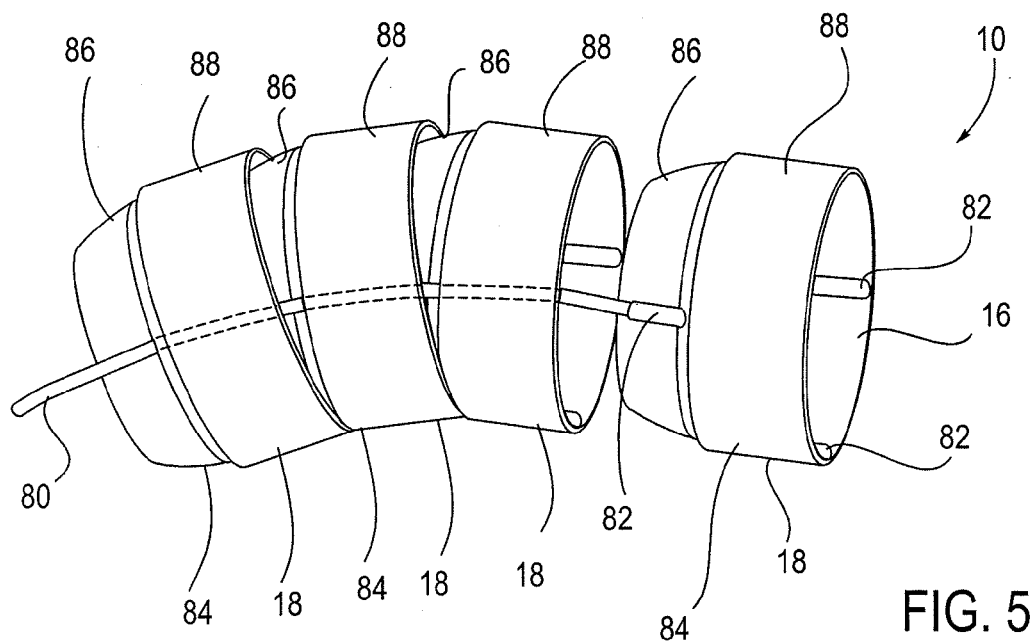
FIG. 5 is a perspective view of the portion of the sheath comprising a series of articulating members.

Referring to FIG. 5, a perspective view of the portion of the shaft 11 comprising a series of articulating members 18 is illustrated. Each articulating member 18 may have any shape, particularly a shape which allows interfitting or nesting as shown. In addition, it is desired that each member 18 have the capability of independently rotating against an adjacent articulating member 18. In this embodiment, the articulating members 18 comprise interfitting domed rings 84. The domed rings 84 each include a base 88 and a dome 86. The base 88 and dome 86 have a hollow interior which, when the domed rings 84 are interfit in a series, forms a central lumen 16. In addition, the dome 86 allows each articulating member 18 to mate against an inner surface of an adjacent domed ring 84. Dome 86 has a convex curvature selected to provide smooth movement and the desired degree of articulation of adjacent domed rings 84. The curvature may be spherical, parabolic, or other rounded shape. Domes 86 could alternatively comprises one or a series of frustoconical surfaces. Base 88 may have a cylindrical, frustoconical, dome-shaped or other suitable external shape.

Also shown in FIG. 5, the interfitting domed rings 84 are connected by at least one pullwire 80. Such pullwires typically extend through the length of the access sheath 10 and at least one of the interfitting domed rings 84 to a fixation point where the pullwire 80 is fixedly attached to the shaft 11. By applying tension to the pullwire 80, the at least one pullwire 80 arcs the series of interfitting domed rings 84 proximal to the attachment point to form a curve. Thus, pulling or applying tension on at least one pullwire, steers or deflects the access sheath 10 in the direction of that pullwire 80. By positioning various pullwires 80 throughout the circumference of the domed rings 84, the access sheath 10 may be directed in any number of directions. Each interfitting domed ring 84 may comprise one or more pullwire lumens 82 disposed around the periphery of each domed ring 84 through which the pullwires 80 are threaded. Alternatively, the pullwires 80 may be threaded through the central lumen 16. In any case, the pullwires are attached to the sheath 10 at a position where a desired curve is to be formed. The pullwires 80 may be fixed in place by any suitable method, such as soldering, gluing, tying, or potting, to name a few. Such fixation method is typically dependent upon the materials used. The articulating members 18 may be comprised of any suitable biocompatible material including stainless steel, cobalt chromium, titanium, various other metals, ceramics, as well as polymers or co-polymers. Likewise the pullwires 80 may be comprised of any suitable material such as fibers, polymeric monofilament or multifilament line, sutures, metal wires, or metal braids. In a preferred embodiment, wires of Nitinol or stainless steel are utilized. Pull wires 80 may be coated with lubricious coatings such as Parylene to reduce friction. Alternatively, sheaths or eyelets (not shown) of low friction material such as Teflon may be provided in lumens 82 or central lumen 16 through which pull wires 80 extend to increase slidability.

In addition, select portions of the articulating members 18 may be fixed together to create desired curves. For example, when the articulating members 18 comprise domed rings 84, two, three, four or more domed rings 84 positioned in a row may be fixed in their interfit positions to prevent movement or rotation between the rings 84. This may be achieved by any suitable method such as soldering, gluing, tying, or potting. Such fixing will create segments which cannot be articulated, however articulating members 18 on either side of these segments may be articulated. This may be useful in creating certain curves or shapes, particularly square shapes or sharp angles. It may also be appreciated that these select portions of articulating members 18 may be fixed to form either a straight segment or a curved segment.

Figures 6A, 6B:
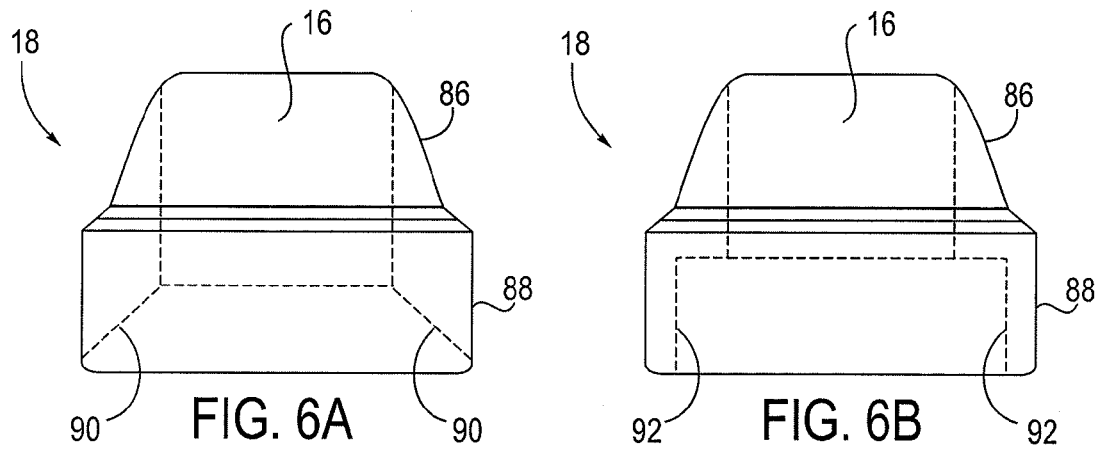
FIGS. 6A-6C are side views of articulating members having different types of inner surfaces.
Figure 6C:
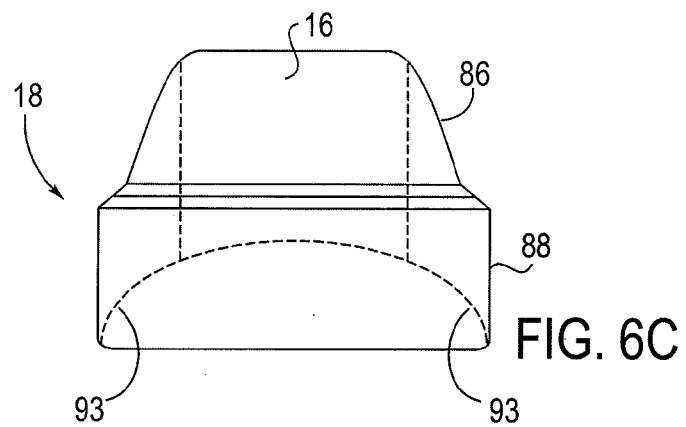

Once the pullwires 80 have been adjusted to obtain a desired articulated position, the series of articulating members 18 may be locked in place to hold the access sheath 10 in the desired articulated position. Such locking is achieved by holding most or all of the pullwires 80 simultaneously to force each articulating member 18 against its neighboring member 18. Locking strength is dependent on a number of variables including shape, material, and surface texture of the articulating members 18. As shown in FIGS. 6A and 6B, the interior shapes of bases 88 and domes 86 are selected to provide the desired strength of locking, degree of articulation, smoothness of movement, and steerability of access sheath 10. As shown in FIG. 6A, a sloping inner surface 90 may be formed on the interior of the domed ring 84. As shown in FIG. 6B, a stepped inner surface 92 may be present on the interior of the domed ring 84. In some cases, the stepped inner surface 92 provides a greater ability to lock tightly, however this may compromise smoothness in steering. As shown in FIG. 6C, a domed inner surface 93 may be present on the interior of the domed ring 84. To increase the locking ability, outer surfaces of the dome 86 and/or the inner surfaces 90, 92, 93 of the base 88 may be textured or coated with materials to increase friction, or a frictional layer may be applied to each dome 86 or a frictional spacer may be positioned between domed rings 84. When the domed rings 84 comprise a metal such as stainless steel, the rings 84 may be sandblasted to increase surface roughness. Alternatively a sandpaper or a steel brush may also be used to increase roughness, or the surfaces may be sintered or have grooves or bumps. When the domed rings 84 comprise an injection molded polymer, a desired roughness may be molded into the surfaces or machined or applied after molding.

Figure 7A:
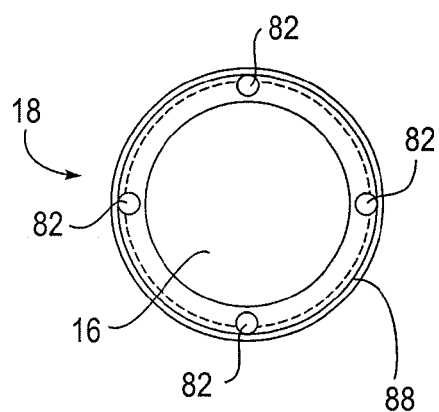
FIGS. 7A-7D illustrate an embodiment of an articulating member which accommodates four pullwires.
Figure 7B:
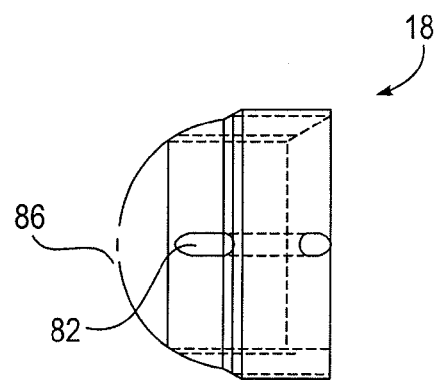
Figure 7C:
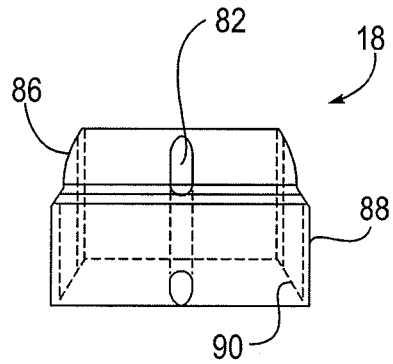
Figure 7D:
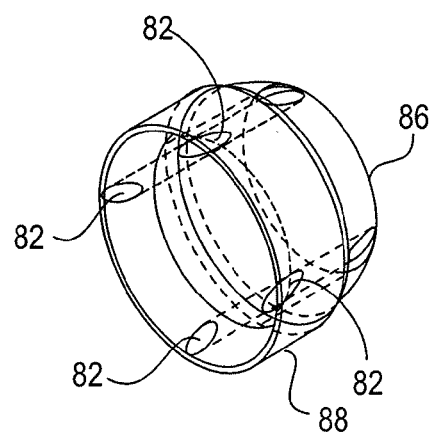

A variety of articulation mechanisms can be used to articulate the access sheath. In preferred embodiments, pullwires 80 are used. Any number of pullwires 80 may be used to articulate the access sheath 10. FIGS. 7A-7D illustrate an embodiment of an articulating member 18 which accommodates such pullwires 80. FIG. 7A is a cross-sectional view of the base 88 of the articulating member 18. Four pullwire lumens 82 are shown equally spaced throughout the wall of the base 88. Such spacing allows curvature of the articulating members in each of the four directions. It may be appreciated that any spacing may be achieved between the pullwire lumens 82 to provide curvature in any desired direction. FIGS. 7B-7C are side views of the member 18 wherein the pullwire lumen 82 is shown to pass through the wall of the base 88 and part of the wall of the dome 86. In this example, the sloping inner surface 90 is shown, however, it may be appreciated that any inner surface contour may be used. FIG. 7B is a perspective view of the articulating member 18 illustrating all four pullwire lumens 82 passing through the base 88 and partially through the dome 86.

Figure 8A:
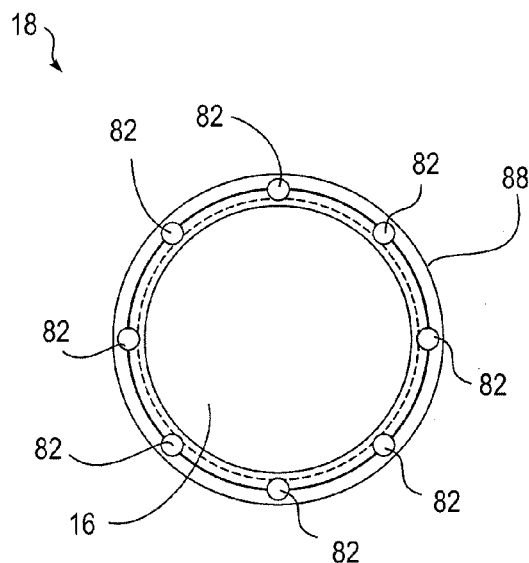
FIGS. 8A-8D illustrate an embodiment of an articulating member which accommodates eight pullwires.
Figure 8B:
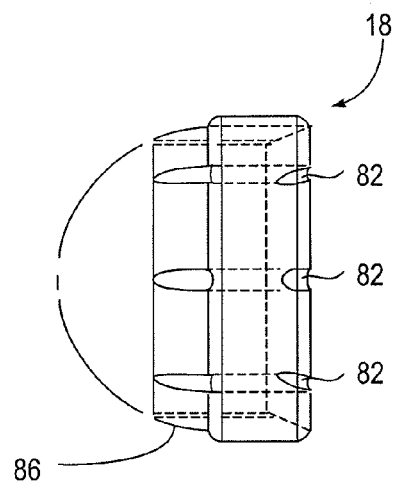
Figure 8C:
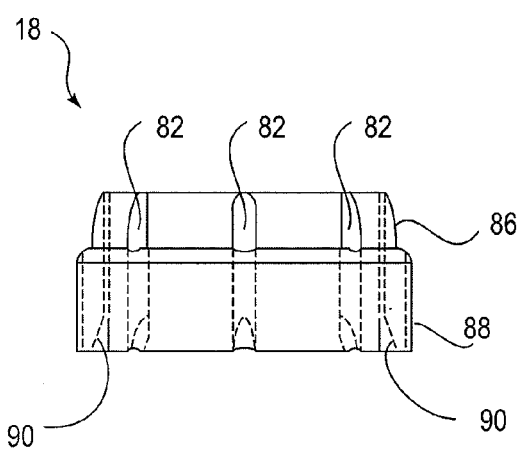
Figure 8D:
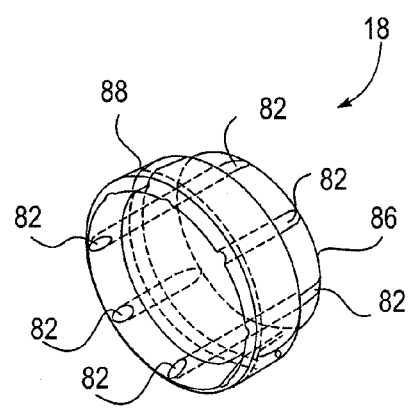
Figure 9A:
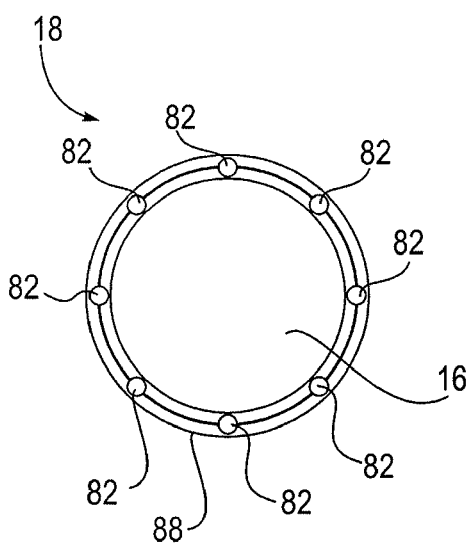
FIGS. 9A-9D illustrate an embodiment of an articulating member which accommodates eight pullwires yet has an inner surface which differs from the embodiment shown in FIGS. 8A-8D.
Figure 9B:
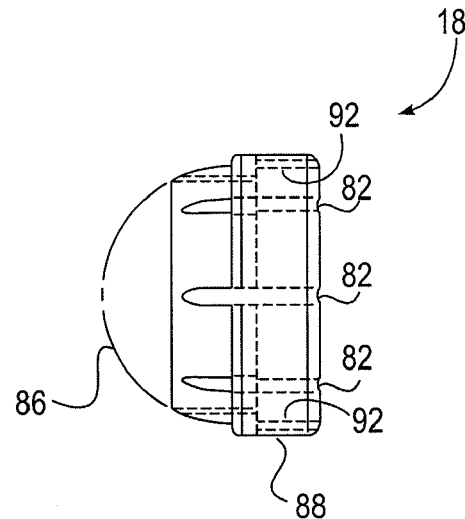
Figure 9C:
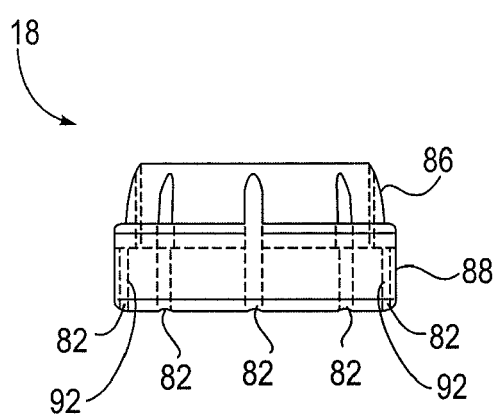
Figure 9D:
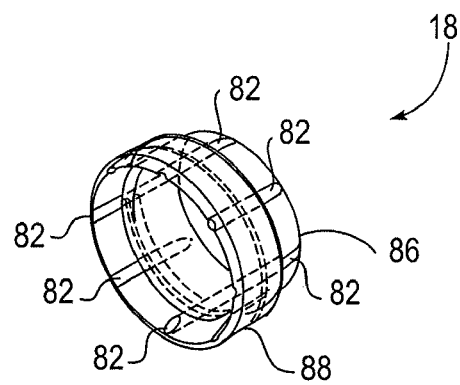

Similarly, FIGS. 8A-8D illustrate an embodiment accommodating eight pullwires. FIG. 8A is a cross-sectional view of the base 88 of the articulating member 18. Eight pullwire lumens 82 are shown equally spaced throughout the circumference of the wall of the base 88. Such number and arrangement of pullwires provides even greater control of the curvature of the access sheath than the embodiment having four pullwires. Again, the lumens may be spaced, sized and arranged to provide any desired curvature. FIGS. 8B-8C are side views of the articulating member 18 having eight pullwire lumens 82. As shown, the pullwire lumens 82 pass through the base 88 and partially through the dome 86. This embodiment also illustrates a sloping inner surface 90. However, it may be appreciated that any type of inner surface may be used, whether it be stepped, tapered, domed, balled or some combination thereof. Similarly, FIGS. 9A-9D illustrate views of an embodiment of the access sheath 10 that includes eight pullwire lumens 82. However, in this case the embodiment shows a stepped inner surface 92 particularly visible in FIGS. 9B-9C.

Figure 10E:
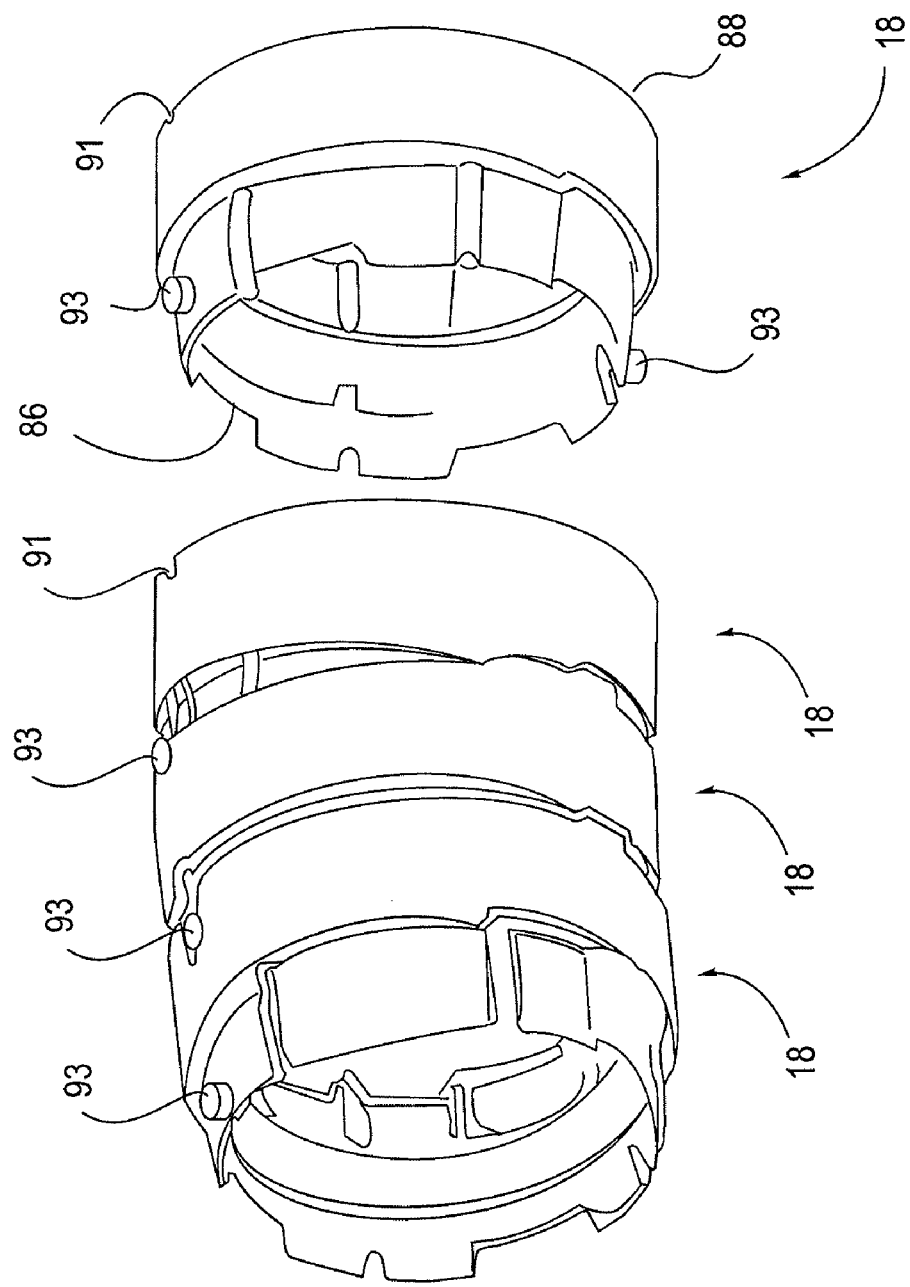

FIGS. 10A-10E illustrate an embodiment of an articulating member 18 which is designed to reduce any possible binding of the pullwires and to increase stability of curves during articulation. To reduce binding of the pullwires during articulation, oblong pullwire lumens 83 are used. As shown in FIG. 10A, a cross-sectional view of the base 88 of the articulating member 18, four circular pullwire lumens 82 are present along with four oblong pullwire lumens 83. The lumens 82, 83 are shown equally spaced and alternating throughout the wall of the base 88. Such spacing allows curvature of the articulating members in each of the four directions. The oblong pullwire lumens 83 allows the pullwires to shift or slide along the lumen 83 to provide more gradual, smoother pathways for the pullwires to follow through the articulating members 18. Oblong pull wire lumens 83 may be of oval, elliptical, arcuate, or a rounded rectangular shape in cross-section, with a length in the circumferential direction substantially longer than the width in the radial direction, usually being at least 1.5 times as long, preferably at least twice as long and in some embodiments at least 3 times as long, and may subtend an arc of at least about 5 degrees, and preferably at least about 20 degrees along the circumference of member 18. FIG. 10B is a side view of the member 18 wherein the circular pullwire lumen 82 is shown to pass through the wall of the base 88 and part of the wall of the dome 86 and the oblong pullwire lumens 83 are shown on either side of the circular pullwire lumen 82. In a preferred embodiment, circular pullwire lumens 82 alternate with oblong pullwire lumens 83 around the circumference of member 18. In this embodiment, dome 86 preferably is divided into a series of annular sections separated by channels in the outer surface thereof, such that contact between adjacent members 18 is limited to the outer surfaces of the annular sections. Some or all of the channels may be axially aligned with oblong pullwire lumens 83. The annular sections of domes 86 preferably subtend an angle of between about 10 and 80 degrees, preferably between about 20 and 45 degrees, along the circumference of members 18.

To increase stability of the curves during articulation, pins are used to keep the members 18 aligned, as illustrated in FIGS. 10C-10E. As shown in FIG. 10C, at least one hole 89 is formed in the wall of the dome 86 and a notch 91 is formed in the base 88. FIG. 10D provides a perspective view of such a hole 89 and notch 91 in the member 18. Typically, as shown, the holes 89 and notches 91 are formed in pairs on opposite sides of the member 18. Referring now to FIG. 10E, pins 93 are inserted into holes 89 and soldered in place. Such pins 93 are typically stainless steel and may have an outer diameter of approximately 0.020 in. and length of approximately 0.030 in. When the members 18 are assembled and interlocked as shown, the notches 91 receive the pins 93. Thus, during articulation, the movement of members 18 is limited to rotation about an axis drawn through pins 93. This stabilizes the device and reduces any rotation in undesired directions.

Liners

Figure 11A:
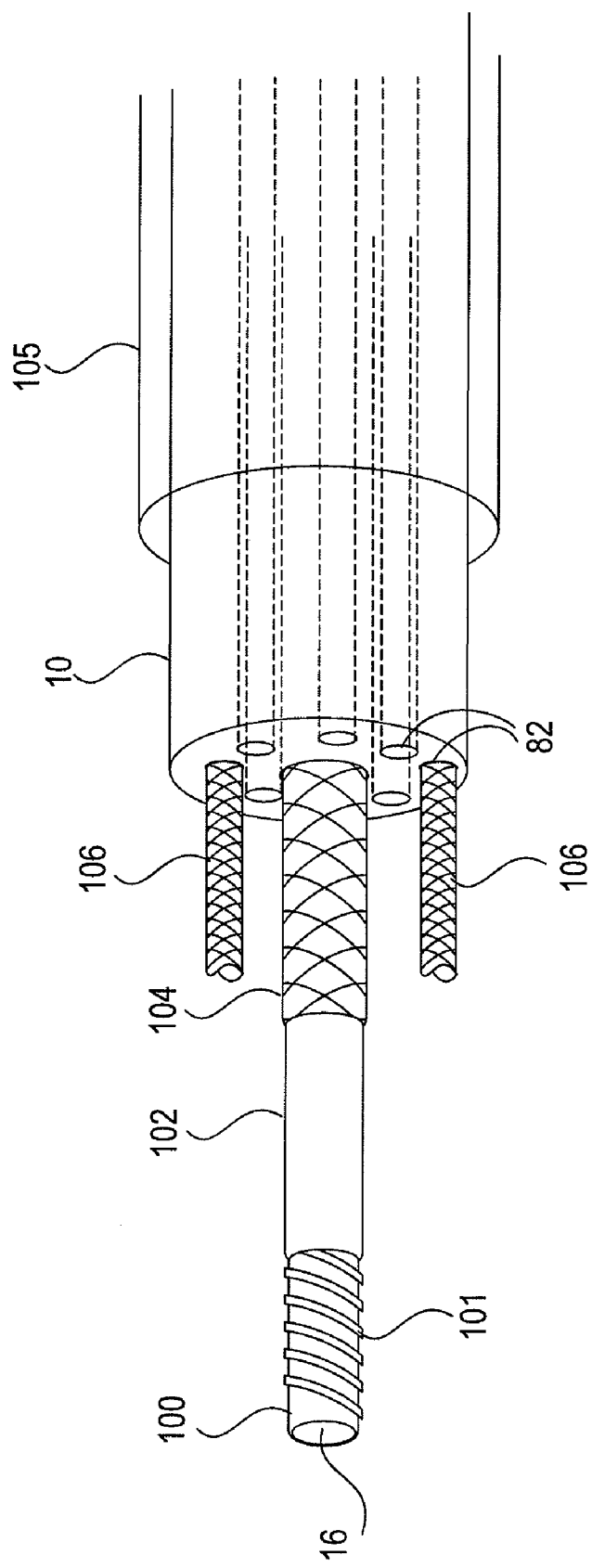
FIG. 11A illustrates various liners which comprise some embodiments of the access sheath.

Referring to FIG. 11A, the access sheath 10 may further comprise various liners which extend through the lumens of the articulating members 18. As shown, a braid 104 may extend through the central lumen 16 of the shaft 11. Such a braid may be comprised of stainless steel or any appropriate material. Typically the braid 104 extends through a length of the shaft 11 to the articulating members 18. The braid 104 provides rigidity and torque response of the shaft 11, proximal to the articulating members 18. Therefore, the braid 104 does not extend within the articulating members 18. Instead, an outer liner 102 and inner liner 100, supported by a coil 101 or similar structure therebetween, extend throughout the length of the articulating members 18. Typically, the coil 101 is comprised of stainless steel or similar material. In some embodiments, the outer liner 102 comprises 35D PEBAX, PTFE, urethane, nylon or polyethylene, to name a few. However, any suitable polymer may be used. Also, in some embodiments, the inner liner 100 is comprised of PTFE or a similar low friction material. Such liners 100, 102 allow an interventional device 70 to be passed through the central lumen 16 without interference with the articulating members 18. In addition, pullwire lumen liners 106 may extend through the pullwire lumens 102 and encapsulate the pullwires 80. Such pullwire lumen liners 106 may be comprised of a braided polyimide or any suitable material to provide strength, flexibility, and protection of the pullwires 80. Finally, in some embodiments, an external liner 105 is positioned over the articulating members and is fused to the inner liner 100 and outer liner 102 at the distal tip. Such an external liner 105 may be comprised of any suitable material, such as PEBAX 35D, and is generally for protection and continuity of the articulating members and as a blood barrier.

Articulation

Figure 11B:
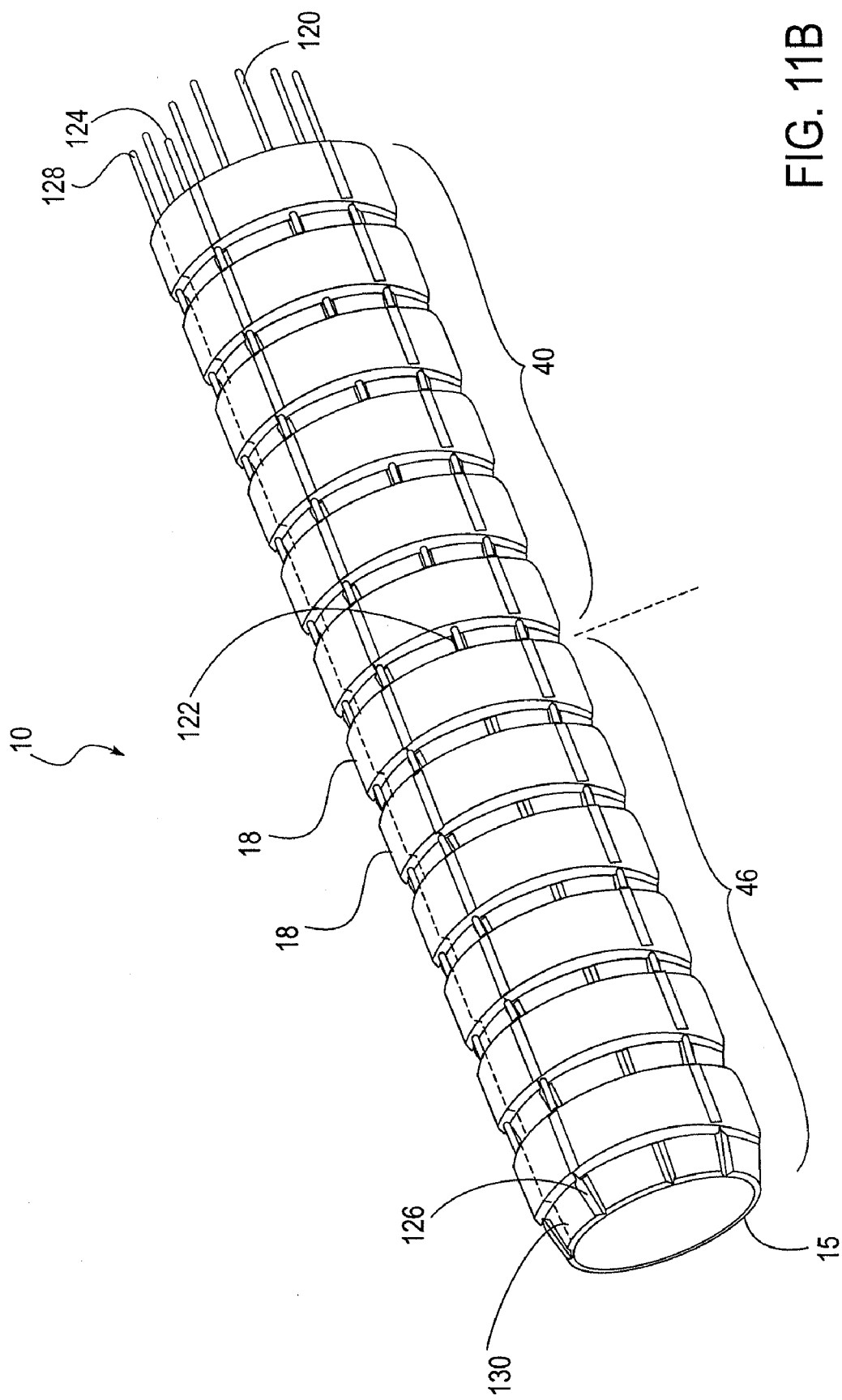
FIG. 11B is a perspective view of an embodiment of an access sheath wherein various pullwires are attached to the shaft at various attachment points.

As described previously, the pullwires 80 pass through the articulating members 18 and attach to the shaft 11 at various attachment points. Referring to FIG. 11B, a first pullwire 120 is shown fixedly attached to the shaft 11 at a primary attachment point 122. Applying tension to the first pullwire 120 arcs the series of articulation members 18 proximal to the primary attachment point 122 to form a primary curve 40. In this example, the primary attachment point 122 is shown midway along the series of articulating members 18. This provides a primary curve 40 proximal to this point 122. It may be appreciated that the primary attachment point 122 may be located anywhere along the shaft 11, including at the distal tip 15. When attached to the distal tip 15, applying tension to the first pullwire 120 would create a primary curve 140 across the entire section of articulating members 18.

In the example illustrated in FIG. 11B, a second pullwire 124 is shown fixedly attached to the shaft 11 at a secondary attachment point 126. Applying tension to the second pullwire 124 arcs the series of articulating members 18 proximal to the secondary attachment point 126 to form a secondary curve 46. Since the first pullwire 120 has already created a primary curve 140 in the proximal section, pulling on the second pullwire 124 creates a secondary curve in a section distal to the proximal section.

Further, a third pullwire 128 may be present which is fixedly attached to the shaft 11 at a distal attachment point 130 so that pulling the third pullwire 128 moves the distal end through an angle theta 50 (see FIG. 4B). Thus, shaft 11, having pullwires 120, 124, 128 which terminate at multiple attachment points 122, 126, 130, respectively, allow the access sheath 10 to be capable of forming a multitude of curves in several different planes.

Access System

Figure 12:
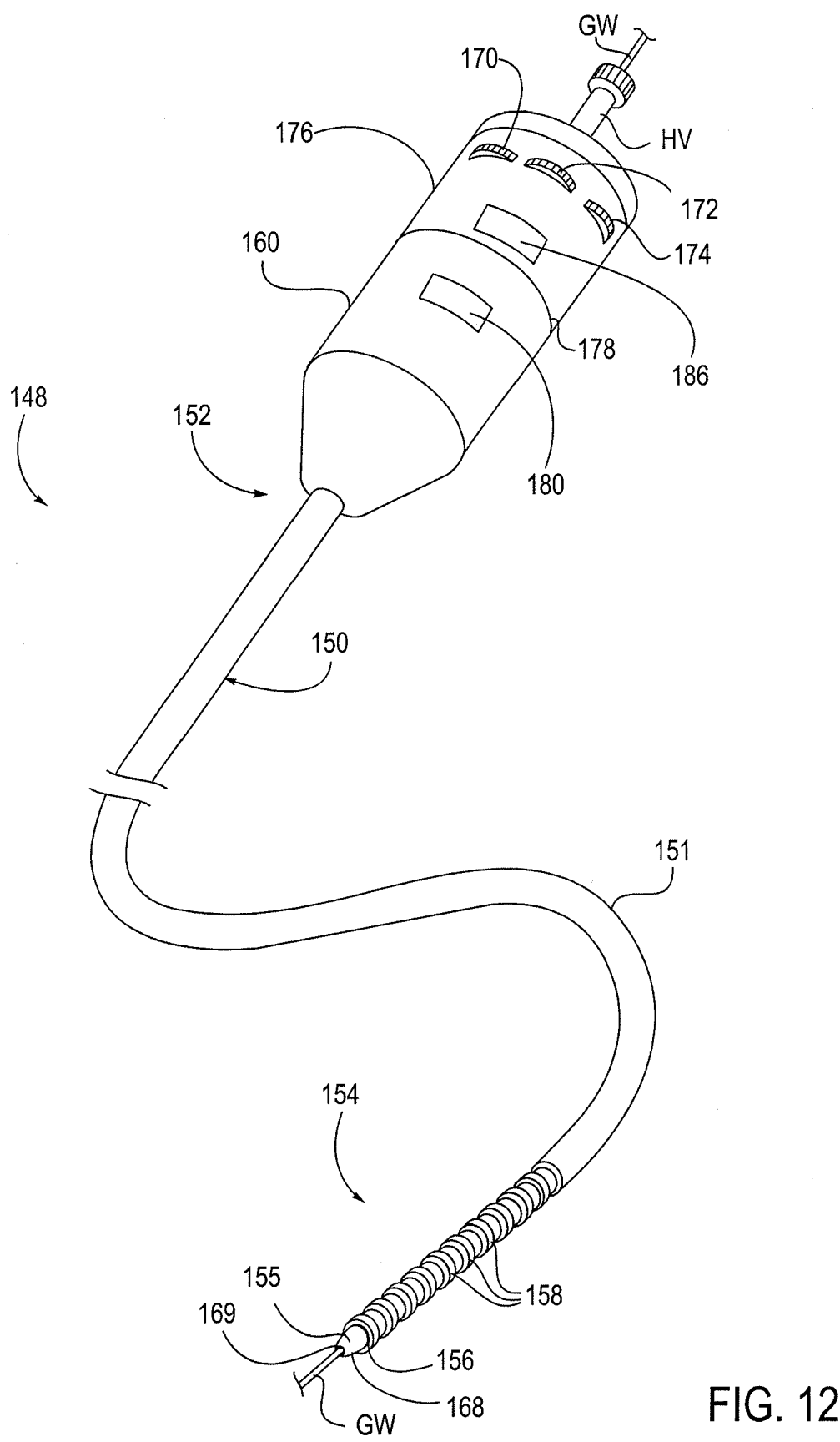
FIG. 12 is a perspective view of an embodiment of an access system of the present invention.

Referring to FIG. 12, an embodiment of an access system 148 of the present invention is illustrated. The access system 148 comprises an access sheath 150 including a shaft 151 having a proximal end 152, a distal end 154, and a central lumen 156 therethrough. The distal end 154 is sized to be passable through a body lumen to a body cavity. Therefore, the distal end 14 preferably has an outer diameter in the range of approximately 0.040 in. to 0.500 in., more preferably in the range of 0.130 in. to 0.300 in. In addition, a portion of the sheath 150 is comprised of a series of articulating members 158. In this embodiment, the articulating members 158 are shown disposed at the distal end 154 of the sheath 150, terminating in a distal tip 155. However, it may be appreciated that the articulating members 158 may be disposed at any location along the sheath. For example, if a straight or non-articulating portion is desired near the distal end 154, the articulating members 158 may be located at a more proximal position. Further, portions of the sheath having articulating members 158 may be interspersed with non-articulating portions, such as in an alternating pattern. A handle 160 is mounted to the proximal end 152 of sheath 150. The access system 148 further comprises an obturator 168 sized for passage through the central lumen 156, as shown. The obturator 168 preferably has an outer diameter in the range of approximately 0.025 in. to 0.440 in., more preferably in the range of 0.115 in. to 0.240 in. Usually, a hemostasis valve of well-known construction (not shown) will be mounted to or within handle 160 in communication with central lumen 156 that allows obturator 168 to be inserted into and removed from central lumen 156 without loss of blood. Obturator 168 may have an axial lumen 169 through which a guidewire GW may be slidably inserted to facilitate guiding access system 148 through the vasculature. If such a guidewire lumen is present, obturator 168 will usually also include a hemostasis valve HV mounted to handle 170 in communication with the guidewire lumen to allow obturator 168 to be slidably introduced over guidewire GW and to allow guidewire GW to be removed from lumen 169 without loss of blood. Guidewire GW, which may be any of various commercially available guidewires, may optionally be included in the system and kits of the invention.

The articulating members 158 of the access sheath 150 may be the same or similar to the articulating members 18 of the articulatable access sheath 10. As mentioned, the articulating members may have any shape, particularly a shape which allows interfitting or nesting as shown in FIG. 5. In addition, pullwires may be present which pass through the articulating members 158 in a manner similar to the pullwire 80 illustrated in FIG. 5. However, the pullwires are not used to position the articulating members 158.

The portion of the sheath 150 having the articulating members 158 is movable into an articulated position by action of the obturator 168 or other device which can fit within the central lumen 156. Once the obturator 168 has been placed within the central lumen 156 of the sheath 150, as shown, the obturator 168 can be moved into any configuration. For example, the obturator 168 can be shaped to have bends, arcs, curves or angles which in turn applies the same configuration to the surrounding sheath 150. Shaping of the obturator 168 can be achieved by any suitable mechanism, such as pullwires which extend through the obturator 158 and can be manipulated in a manner similar to the articulatable access sheath 10. Thus, the sheath 150 and obturator 168 can be moved into articulated positions similar to those shown in FIGS. 2A-2D.

Actuation of the positioning mechanisms is achieved with the use of actuators, such as actuators 170, 172, 174 located on an obturator handle 176. The obturator handle 176 may be connectable to a handle 160 of the sheath 150 at a connection joint 178. The actuators 170, 172, 173 are used to bend, arc or reshape the obturator 168 underlying the portion of the sheath 150 comprising articulating members 158. For example, a primary curve actuator 170 can be used to actuate one or more pull wires to form a primary curve in the portion of the sheath 150 comprising the series of articulating members 158. Further, a secondary curve actuator 172 can be actuated to form a secondary curve in the portion of the sheath 150 comprising the series of actuating members 158. And a theta actuator 174 can be manipulated to move the distal tip 155 through an angle theta.

Once the sheath 150 is in the desired configuration, a locking actuator 180 on the handle 160 may be used to actuate a locking mechanism to lock the articulating members 158 in the articulated position. Optionally, the obturator 168 may also be locked in place by an obturator locking mechanism actuated by an obturator locking actuator 186. Typically, the obturator 168 would be locked in place prior to the sheath 150 to hold the sheath in the desired orientation. Once the sheath 150 is then locked, the obturator 168 may be unlocked and removed. Again, it may be appreciated that such actuators 170, 172, 174, 180, 186 and any additional actuators located on the handles 160, 176 may take any suitable form including knobs, buttons, levers, switches, toggles, sensors or other devices. In addition, the handles 160, 176 may include a numerical or graphical display of information such as data indicating the articulated position of the sheath 150 and/or obturator 168.

Figure 13A:
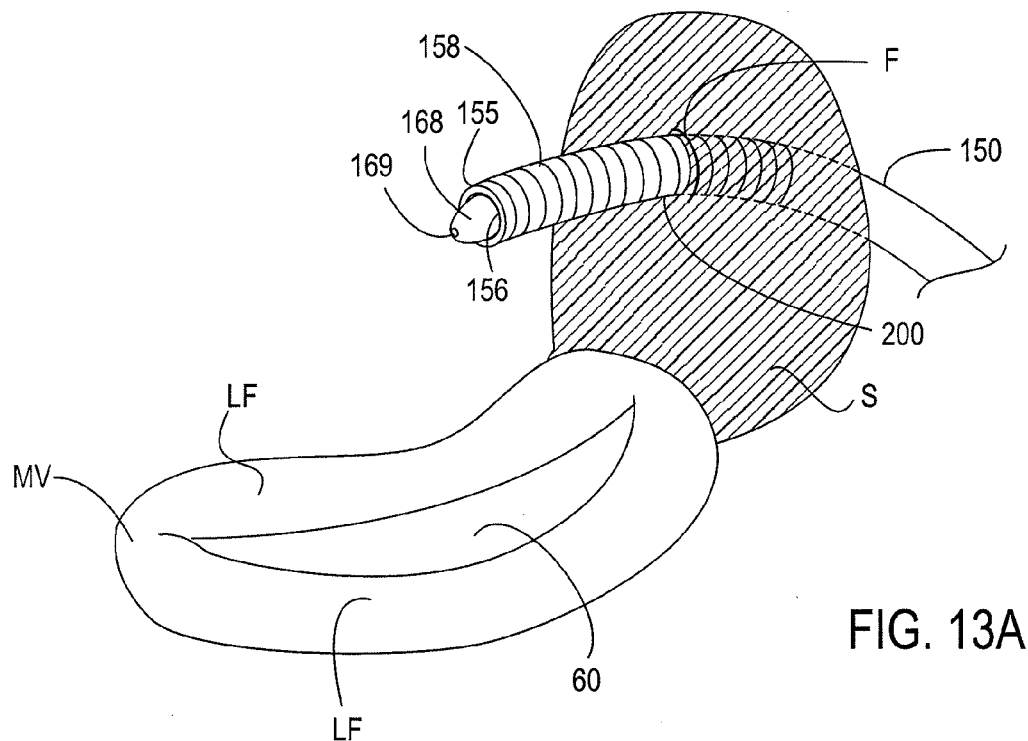
FIGS. 13A-13D illustrate a method of using the access system for accessing the mitral valve.

FIGS. 13A-13D illustrate a method of using the access system 148 for accessing the mitral valve MV. To gain access to the mitral valve, the access system 148 may be tracked from a puncture in the femoral vein, through the interior vena cava and into the right atrium. This may be facilitated by the use of a guidewire that is first inserted through the vasculature into the heart, and sheath 150 and obturator 168 are then slidably introduced over the guidewire. Preferably, obturator 168 will have a guidewire lumen for this purpose as described above. As shown in FIG. 13A, the access system 148 is then punctured through a fossa F in the intra-atrial septum S. Obturator 168 may further have a distal tip configured to penetrate the inter-atrial septum S, or obturator 168 may be removed and a separate penetration tool may be inserted though the access sheath 150. Alternatively, if a guidewire is used, the guidewire may have a tip suitable for penetrating the inter-atrial septum and the distal tip of obturator 168 may be tapered to facilitate widening the guidewire penetration so as to allow passage of sheath 150. The system 148 is then advanced through the fossa F so that the distal tip 155 is directed over the mitral valve MV. Again, it may be appreciated that this approach serves merely as an example and other approaches may be used, such as through the jugular vein, femoral artery, port access or direct access, to name a few. It may also be appreciated that the sheath 150 and obturator 168 of the system 148 may alternatively be advanced in separate steps.

It is then desired to move and tip the distal tip 155 so that the central lumen 156 is directed toward the target tissue, the mitral valve MV. In particular, the central lumen 156 is to be directed toward a specific area of the mitral valve MV, such as toward the opening 60 between the valve leaflets LF, so that a particular interventional procedure may be performed. A primary curve 200 may be formed due to actuation of the obturator 168, as described above. The obturator 168 applies forces to the central lumen 156 to reposition the articulating members 158. In this example, formation of the primary curve 200 moves the distal tip 155 within a primary plane, corresponding to previous plane X in FIG. 2A, parallel to the valve surface. This moves the distal tip 155 laterally along the short axis of the mitral valve MV, and allows the distal tip 155 to be centered over the opening 60. In this articulated position, any interventional devices which are passed through the central lumen 16 would be directed horizontally over the valve MV. To direct catheters or tools into the opening 60, it is necessary that the distal tip 155 is pointed downward towards the mitral valve MV.

Figure 13B:
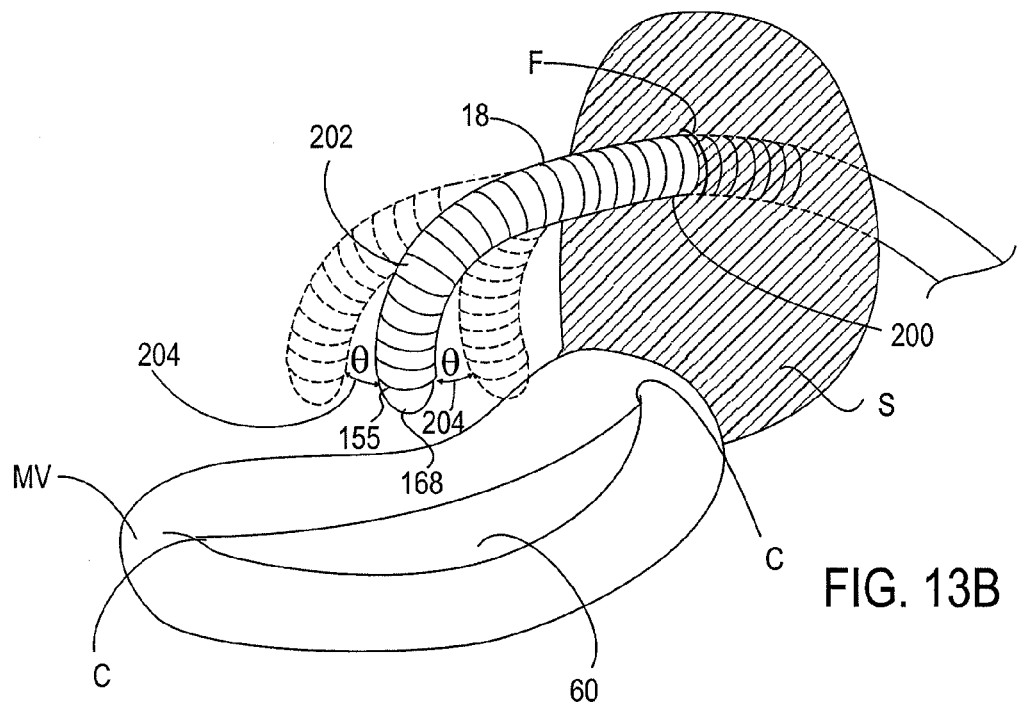

Referring to FIG. 13B, the access sheath 150 is shown in an articulated position which includes a secondary curve 202 in a secondary plane, corresponding to previous plane Z in FIG. 2B. Formation of the secondary curve 202 moves the distal tip 15 vertically and angularly between the commissures C, directing the central lumen 156 toward the mitral valve MV. In this articulated position an interventional device which is passed through the central lumen 156 would be directed toward and/or through the opening 60. Although the primary curve 200 and the secondary curve 202 may be varied to accommodate different anatomical positions of the valve MV and different surgical procedures, further adjustment may be desired beyond these two curvatures for proper positioning of the access sheath 150.

Thus, the access sheath 150 may include additional curvatures throughout the articulating members 158 and/or allow the distal tip 155 to move angularly through an angle theta 204 by action of the obturator 168. This moves the tip 155 vertically and angularly through a theta plane, corresponding to previous plane Y in FIG. 2C-2D. Movement of the distal tip 155 through the angle theta 50 in either direction is shown in dashed line in FIG. 13B. Consequently, the central lumen 156 can be directed toward the mitral valve MV within a plane which differs from the secondary plane. After such movements, the access sheath 150 will be in an articulated position which positions the distal tip 15 so that the opening of the central lumen 156 at the tip 155 faces the desired direction. Once the desired articulated position is achieved, the articulating members 158 are then locked in place by a locking feature, such as by activation of a locking mechanism.

Figure 13C:
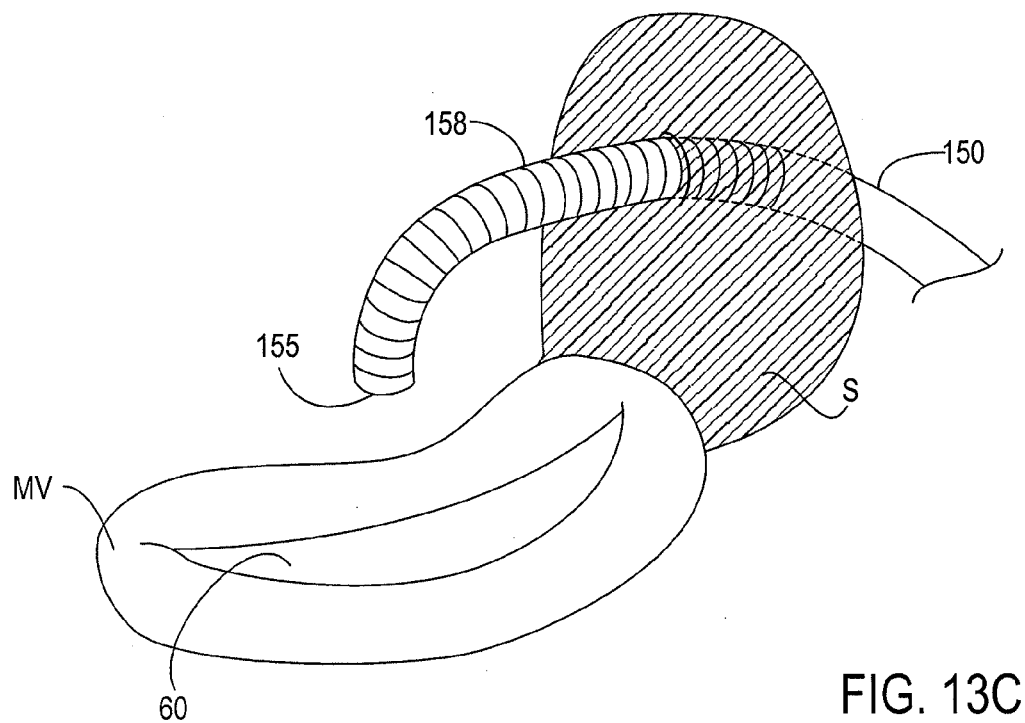
Figure 13D:
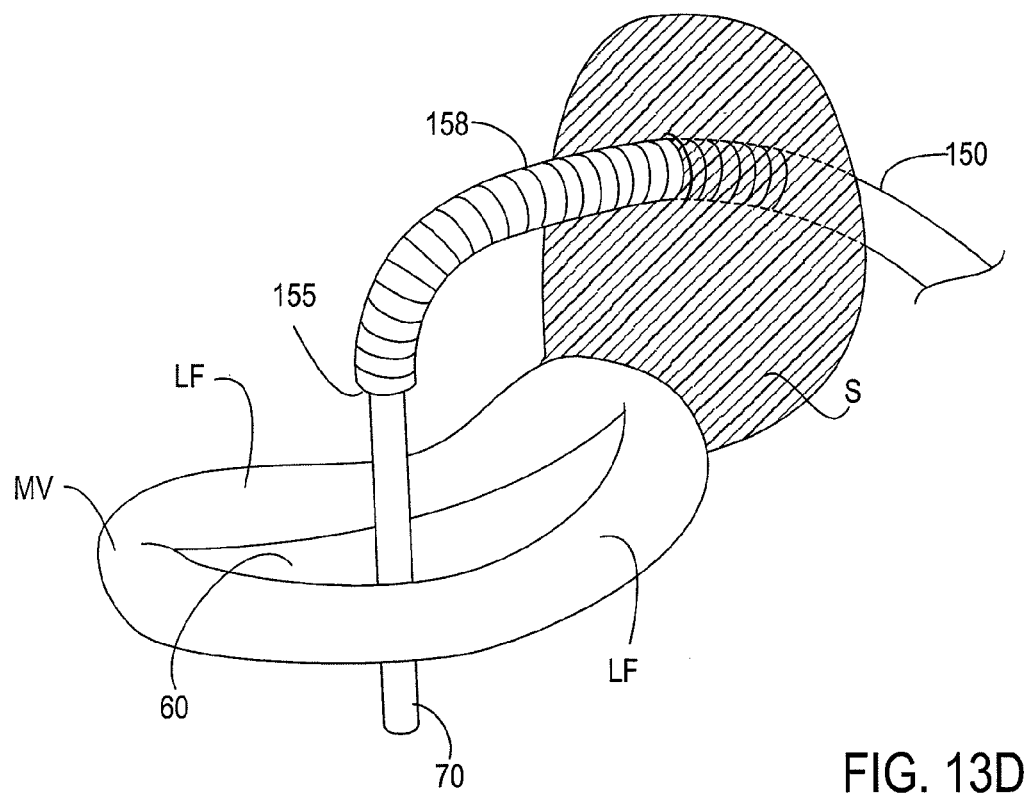

Referring to FIG. 13C, the obturator 168 is then removed while the sheath 150 remains in the articulated position. The locked access sheath 150 allows for the passage of interventional devices 70, as illustrated in FIG. 13D. The interventional device 70 can be passed through the central lumen 156 toward the target tissue, in this case the mitral valve MV. Positioning of the distal end 155 over the opening 60, as described above, allows the device 70 to pass through the opening 60 between the leaflets LF if desired, as shown. At this point, any desired surgical procedure may be applied to the mitral valve for correction of regurgitation or any other disorder. In a preferred method, the mitral valve is repaired using a "bow-tie" or "edge-to-edge" technique with devices introduced through the access sheath of the invention. Suitable devices and techniques are described in copending U.S. patent application Ser. No. 10/441,531, U.S. patent application Ser. No. 10/441,508, and U.S. patent application Ser. No. 10/441,687, which have been incorporated herein by reference. Other procedures that may be performed using devices introduced through the access sheath of the invention include ablation of the pulmonary veins for treatment of atrial fibrillation, mapping and ablation of other regions in or on the heart, annuloplasty of the mitral valve, repair of other heart valves, repair of septal defects, and other diagnostic and therapeutic procedures in the heart. The access sheath of the invention is further suitable for accessing and performing procedures on other organs of the body either intraluminally or via surgical penetrations, including stomach, intestines, bowel, bladder, lungs, liver, gall bladder, uterus, and others.

It may be appreciated that in some embodiments both the obturator 168 and the sheath 150 are independently steerable. In these embodiments, the obturator 168 and sheath 150 can be shaped or articulated by any suitable mechanism, such as pullwires which extend through the obturator 158 and separate pullwires which extend through the sheath 150 and can be manipulated to create bends, arcs, curves or angles. Thus, the sheath 150 and obturator 168 can be moved into articulated positions similar to those shown in FIGS. 2A-2D.

Figure 14:
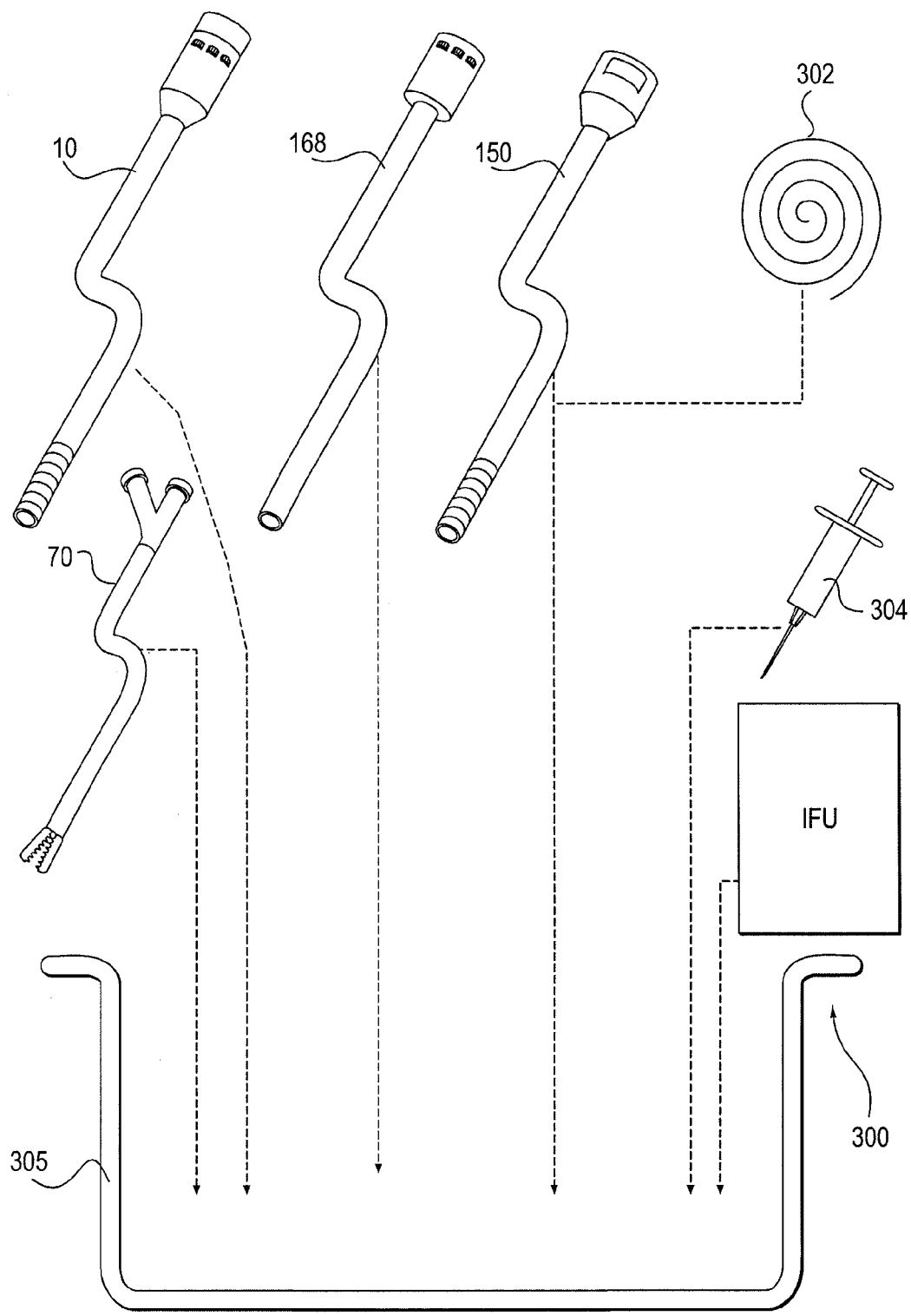
FIG. 14 illustrates a kit constructed in accordance with the principles of the present invention.

Referring now to FIG. 14, kits 300 according to the present invention comprise any of the components described in relation to the present invention. In some embodiments, the kit 300 comprises an articulatable access sheath and instructions for use IFU. In other embodiments, the kit 300 comprises an access sheath 150, an articulatable obturator 168 and instructions for use IFU. Optionally, any of the kits may further include any of the other system components described above, such as an interventional device 70, or components associated with positioning a device in a body lumen, such as a guidewire 302 or needle 304. The instructions for use IFU will set forth any of the methods as described above, and all kit components will usually be packaged together in a pouch 305 or other conventional medical device packaging. Usually, those kit components which will be used in performing the procedure on the patient will be sterilized and maintained within the kit. Optionally, separate pouches, bags, trays or other packaging may be provided within a larger package, where the smaller packs may be opened separately to separately maintain the components in a sterile fashion.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. An articulatable access system for accessing a chamber of a heart, said system comprising:
    a shaft having a proximal end, a distal end, and a central lumen therethrough, the central lumen having proximal and distal openings, wherein a portion of the shaft comprises a series of articulating members defining a distal region near the distal end, a proximal region proximal to the distal region, and a middle region therebetween, wherein the distal end is passable through to the body cavity and wherein the central lumen and the distal opening are sized for passage of an interventional device to act on a heart valve;
    a first set of pullwires operably coupled with the proximal region at a primary attachment location such that applying tension to the first set of pullwires deflects the articulating members to form a primary curve proximal to the primary attachment location, the primary curve having a first radius;
    a second set of pullwires operably coupled with the middle region at a secondary attachment location such that applying tension to the second set of pullwires deflects the articulating members to form a secondary curve proximal to the secondary attachment location, the secondary curve distal to the primary curve and having a secondary radius different than the first radius; and
    a third set of pullwires operably coupled with the distal region at a distal attachment location such that applying tension to the third set of pullwires moves the distal end of the shaft through an angle theta,
    wherein at least some of the pullwires extend through one or more pullwire lumens disposed in one or more of the articulating members, at least some of the pullwire lumens adapted to reduce binding of the pullwire passing therethrough,
    wherein the shaft is configured to navigate toward the chamber of the heart to position the interventional device to act on the heart valve.

2. The system of claim 1, further comprising a locking mechanism to hold the articulating members in a fixed articulated position to direct the device to the chamber of the heart.

3. The system of claim 2, wherein the locking mechanism comprises means for holding at least one of the pullwires in a tensioned position so that the articulating members are compressed together.

4. The system of claim 2, wherein the locking mechanism comprises a frictional surface on at least a portion of the articulating members to enhance friction between the articulating members.

5. The system of claim 1, wherein the primary curve has a radius of curvature in the range of approximately 0.125 inches to 1.000 inches.

6. The system of claim 1, wherein the secondary curve has a radius of curvature in the range of approximately 0.050 inches to 0.750 inches.

7. The system of claim 1, wherein the primary curve and secondary curve lie in different planes.

8. The system of claim 7, wherein the primary curve and secondary curve lie in substantially orthogonal planes.

9. The system of claim 1, wherein the distal region terminates in a distal tip and the third set of pullwires is fixedly attached to the distal tip to allow the distal tip to move through the angle theta.

10. The system of claim 9, wherein the secondary curve and the angle theta lie in different planes.

11. The system of claim 10, wherein the secondary curve and the angle theta lie in orthogonal planes.

12. The system of claim 9, wherein the primary curve, secondary curve and the angle theta each lie in different planes.

13. The system of claim 12, wherein the primary curve, secondary curve and the angle theta each lie in orthogonal planes.

14. The system of claim 1, wherein distal end is configured to be passable through a blood vessel.

15. The system of claim 1, wherein at least some of the pullwire lumens have a cross-section that subtends an arc of at least 5° circumferentially along the articulatable members.

16. The system of claim 1, wherein at least some of the pullwires in either the first set, the second set, or the third set, are coated with a lubricious coating.

17. The system of claim 1, wherein the first set of pullwires comprises a pair of pullwires operably coupled with the articulating members.

18. The system of claim 1, wherein the second set of pullwires comprises a pair of pullwires operably coupled with the articulating members.

19. The system of claim 1, wherein the third set of pullwires comprises a pair of pullwires operably coupled with the articulating members.

20. The system of claim 1, wherein the articulating members comprise interfitting domed rings.

21. The system of claim 20, wherein a first interfitting domed ring comprises a notch, and an adjacent interfitting domed ring comprises an aperture disposed therein, the system further comprising a pin disposed in the notch and in the aperture, thereby limiting movement of the first interfitting domed ring relative to the adjacent interfitting domed ring to rotation about a longitudinal axis of the pin.

22. The system of claim 1, wherein each of the articulating members is independently rotatable against an adjacent articulating members.

23. The system of claim 1, wherein the angle theta is in the range of −100° to +100° degrees.

24. The system as in claim 1, further comprising an obturator removably positioned in the central lumen.

25. The system of claim 24, wherein the obturator is flexible such that the shaft is positionable through the patient's vasculature when the obturator is positioned in the central lumen.

26. The system of claim 24, wherein the obturator is configured to position the portion of the shaft into a first shape.

27. The system of claim 24, wherein the obturator further comprises a guidewire lumen configured to slidably receive a guidewire.

28. The system of claim 26, wherein the obturator is generally straight such that the first shape is generally straight.

29. The system of claim 26, wherein the obturator is articulatable such that the first shape has at least one curve.

30. The system of claim 24, further comprising a hemostasis valve in communication with the central lumen, and adapted to inhibit fluid flow therefrom, the hemostasis valve being configured to receive the interventional device and the obturator.

* * * * *